United States Patent
Fujioka et al.

(10) Patent No.: US 10,031,083 B2
(45) Date of Patent: Jul. 24, 2018

(54) FIXED POSITION CONTROLLER AND METHOD

(71) Applicant: HITACHI HIGH-TECHNOLOGIES CORPORATION, Tokyo (JP)

(72) Inventors: Michiru Fujioka, Tokyo (JP); Tsuyoshi Sonehara, Tokyo (JP); Naoshi Itabashi, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/518,341

(22) PCT Filed: Oct. 16, 2014

(86) PCT No.: PCT/JP2014/077550
§ 371 (c)(1),
(2) Date: Apr. 11, 2017

(87) PCT Pub. No.: WO2016/059703
PCT Pub. Date: Apr. 21, 2016

(65) Prior Publication Data
US 2017/0307532 A1    Oct. 26, 2017

(51) Int. Cl.
*G01J 3/44*        (2006.01)
*G01N 21/65*       (2006.01)
(Continued)

(52) U.S. Cl.
CPC ..... *G01N 21/658* (2013.01); *G01N 33/48721* (2013.01); *G01Q 60/22* (2013.01);
(Continued)

(58) Field of Classification Search
CPC ........... G01N 21/658; G01N 33/48721; G01Q 60/22; G11B 7/08; G11B 7/1387; G11B 7/08576; G11B 7/22; G11B 23/0318
(Continued)

(56) References Cited

U.S. PATENT DOCUMENTS

| 4,807,159 A | 2/1989 | Komatsu et al. |
| 2002/0105723 A1 | 8/2002 | Bewersdorf et al. |

(Continued)

FOREIGN PATENT DOCUMENTS

| JP | 1987-043050 A | 2/1987 |
| JP | 2002-214536 A | 7/2002 |

(Continued)

OTHER PUBLICATIONS

International Search Report for WO 2016/059703 A1, dated Jan. 27, 2015.

*Primary Examiner* — Hina F Ayub
(74) *Attorney, Agent, or Firm* — Volpe and Koenig, P.C.

(57) ABSTRACT

The purpose of the present invention is to control, with a simple structure and high accuracy, irradiation of excitation light to a multi-nanopore substrate without interrupting a measurement. Irradiation of excitation light is performed concurrently to at least one nanopore and at least one reference object on a substrate mounted in an observation container 103. A position irradiated with the excitation light in a measurement sample is calculated on the basis of a signal generated from the reference object detected by a detector 109, and the measurement and a fixed position control is performed concurrently by performing measurement of the measurement object while a drive control part 115 controlling the position of the irradiation of the excitation light to the measurement sample on the basis of the calculation result, whereby an analysis of the measurement sample can be performed in a short time.

15 Claims, 11 Drawing Sheets

(51) Int. Cl.
*G01N 33/487* (2006.01)
*G01Q 60/22* (2010.01)
*G11B 23/03* (2006.01)
*G11B 7/08* (2006.01)
*G11B 7/1387* (2012.01)
*G11B 7/085* (2006.01)
*G11B 7/22* (2006.01)

(52) U.S. Cl.
CPC .............. *G11B 7/08* (2013.01); *G11B 7/1387* (2013.01); *G11B 23/0318* (2013.01); *G11B 7/08576* (2013.01); *G11B 7/22* (2013.01)

(58) Field of Classification Search
USPC ........................................................ 356/301
See application file for complete search history.

(56) References Cited

U.S. PATENT DOCUMENTS

| | | | |
|---|---|---|---|
| 2005/0118640 A1 | 6/2005 | Kureshy et al. | |
| 2013/0128025 A1 | 5/2013 | Dyba et al. | |
| 2013/0176563 A1 | 7/2013 | Ozawa et al. | |

FOREIGN PATENT DOCUMENTS

| | | |
|---|---|---|
| JP | 2003-172684 A | 6/2003 |
| JP | 2005-527827 A | 9/2005 |
| JP | 2013-533513 A | 8/2013 |
| WO | 2012/043028 A1 | 4/2012 |

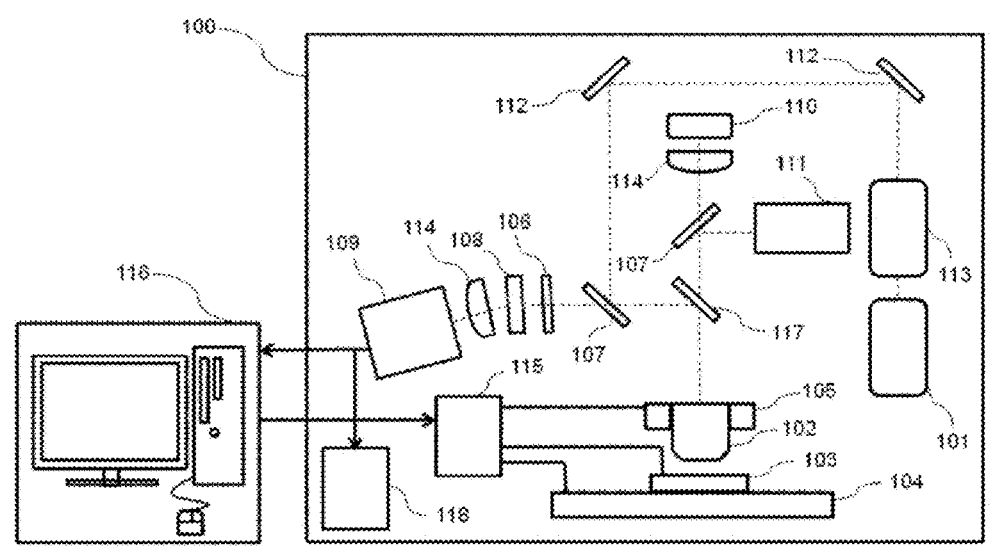
[Fig. 1]

[Fig. 2]
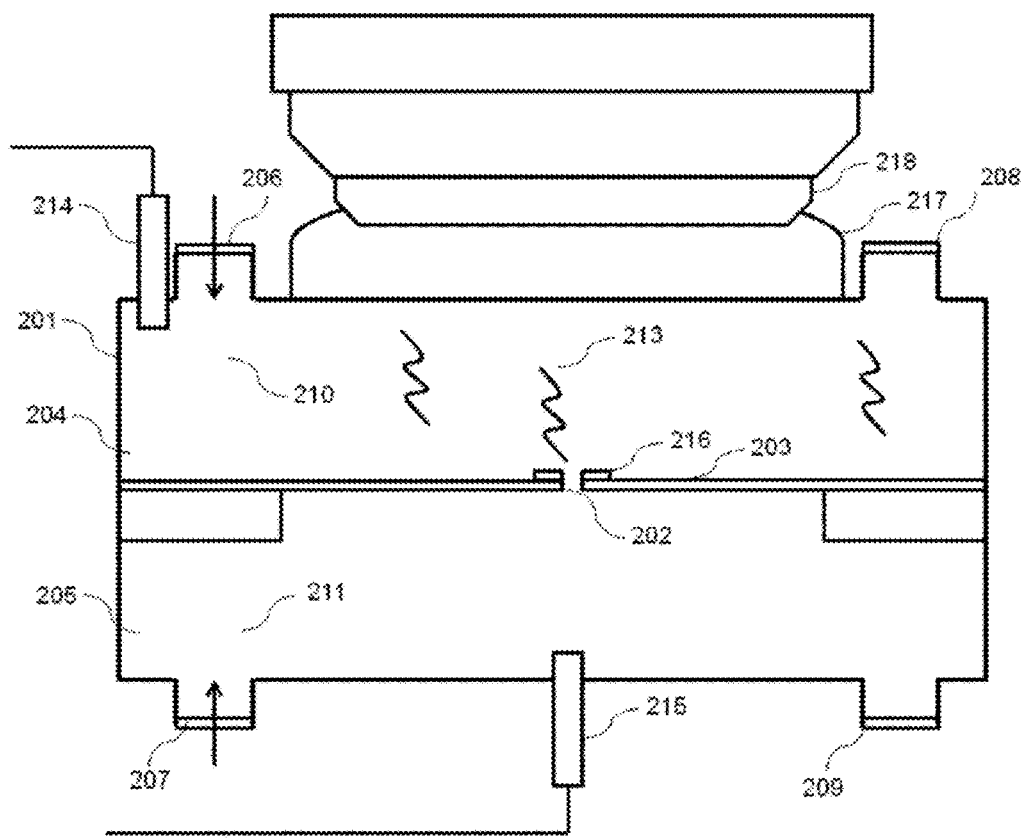

[Fig. 3]
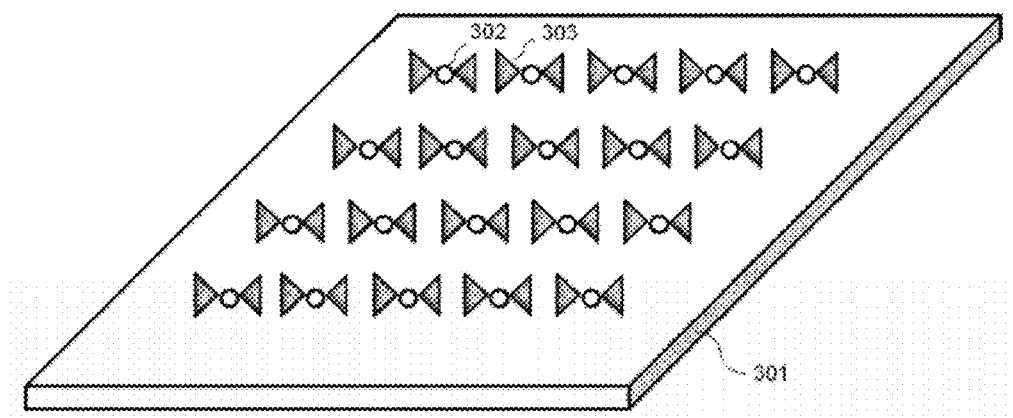
[Fig. 4A]
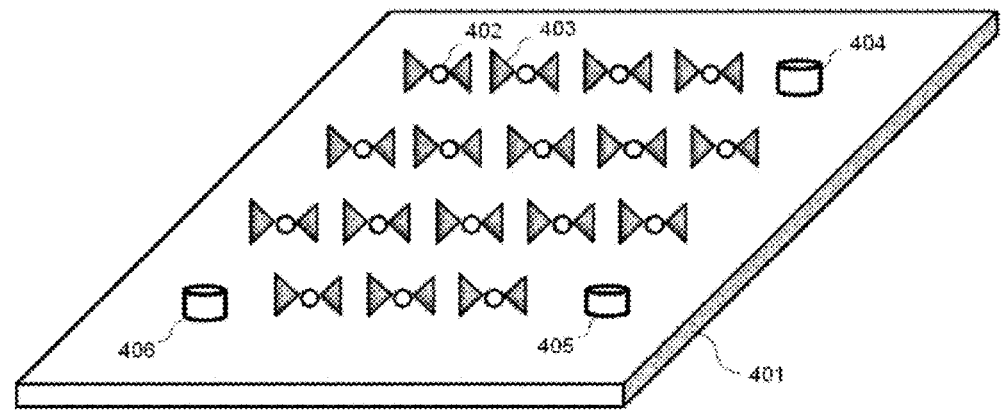

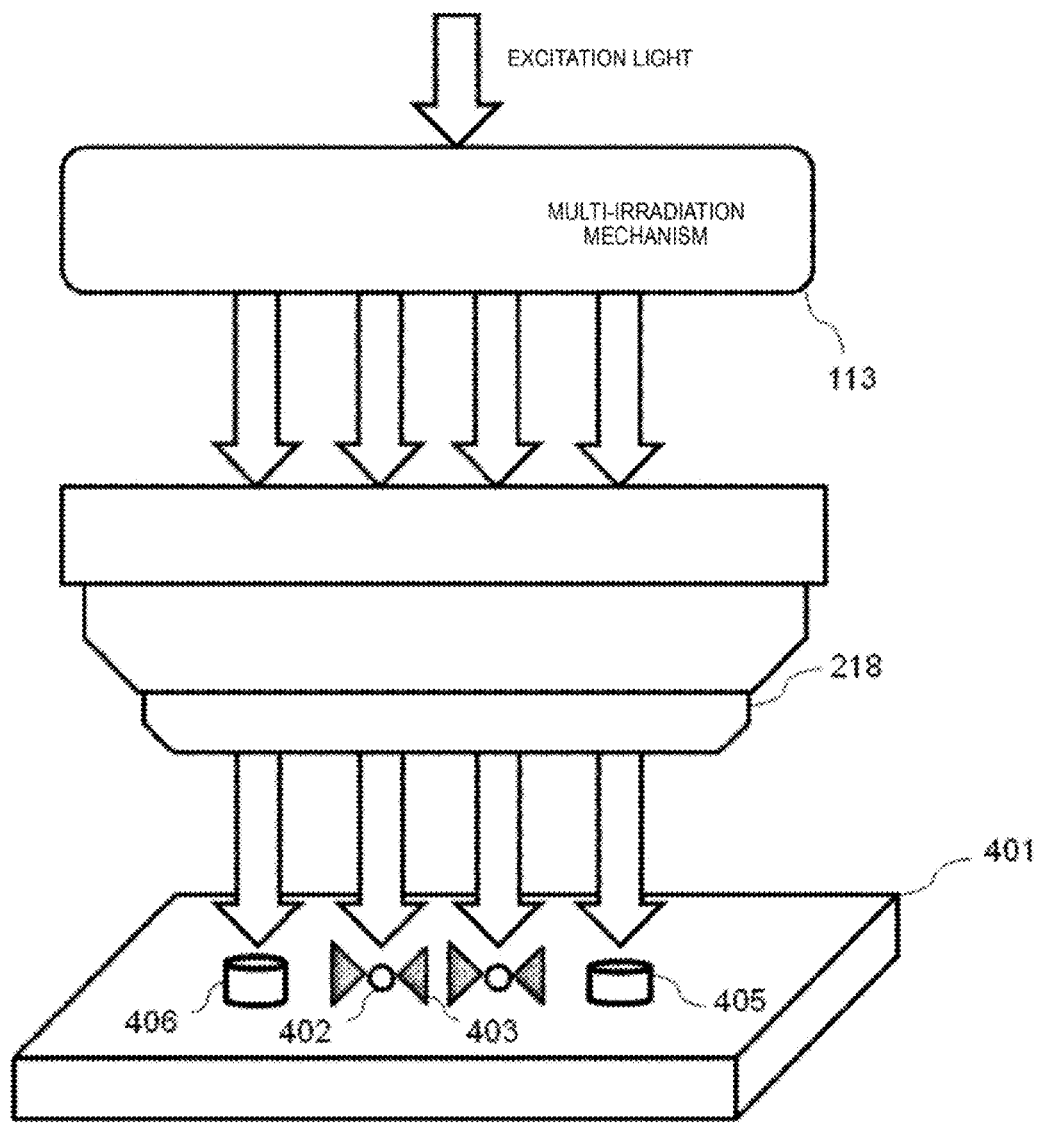
[Fig. 4B]

[Fig. 5]
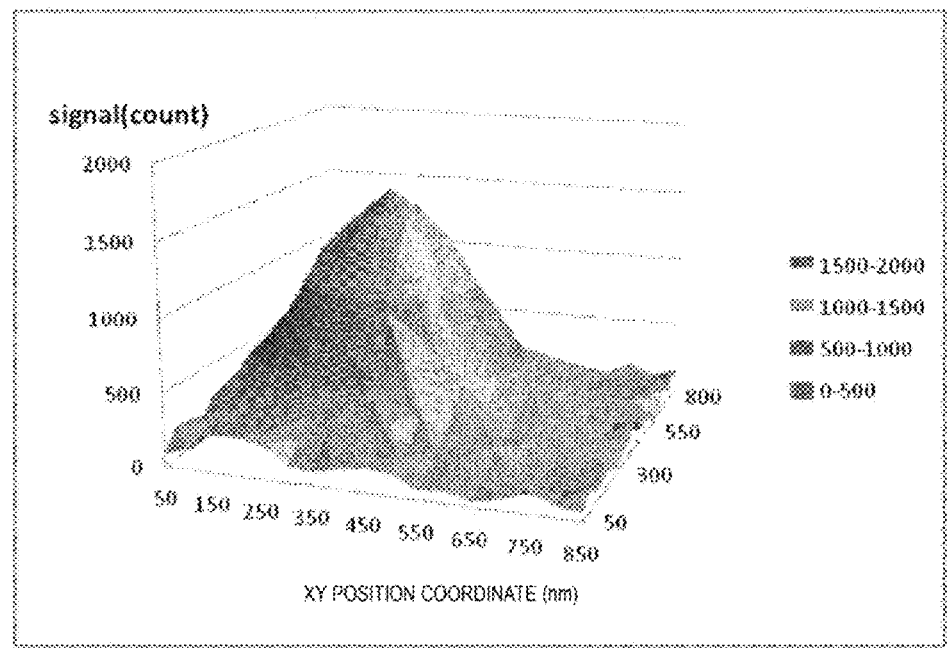
[Fig. 6]
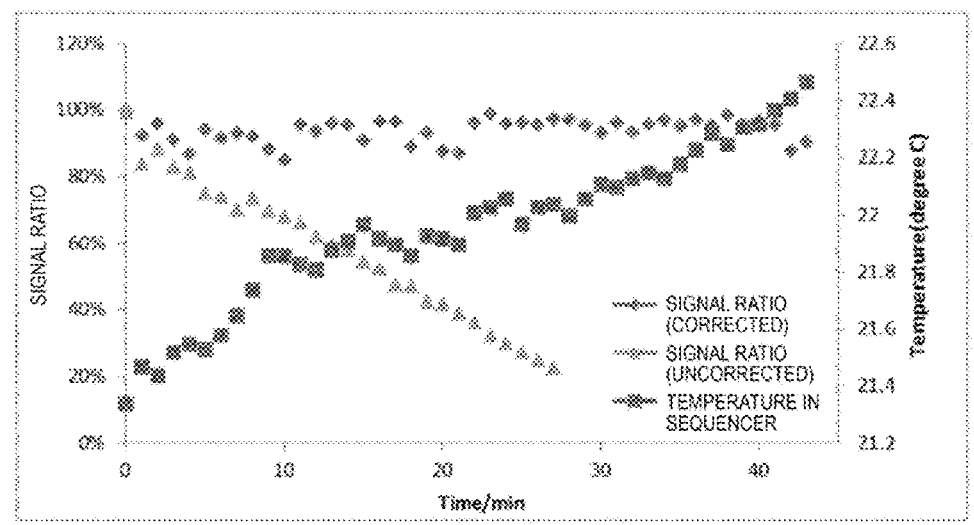

[Fig. 7]
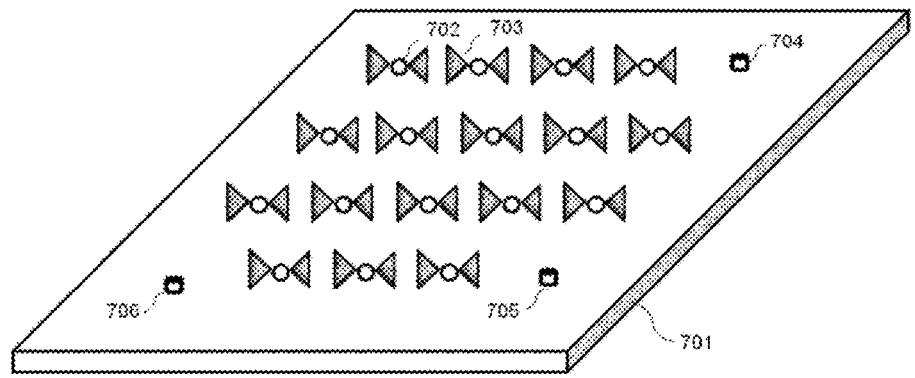
[Fig. 8]
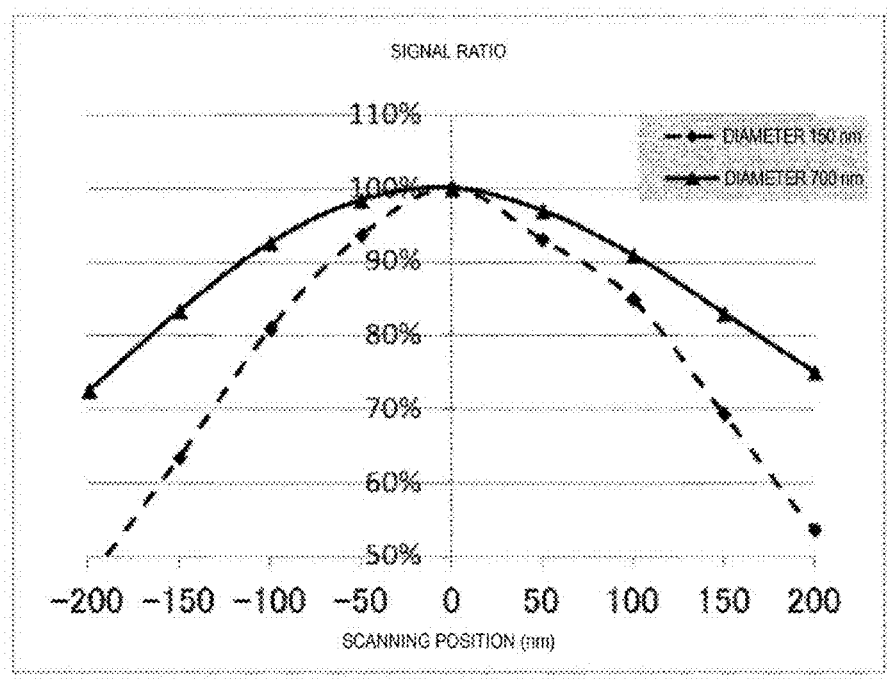

[Fig. 9]
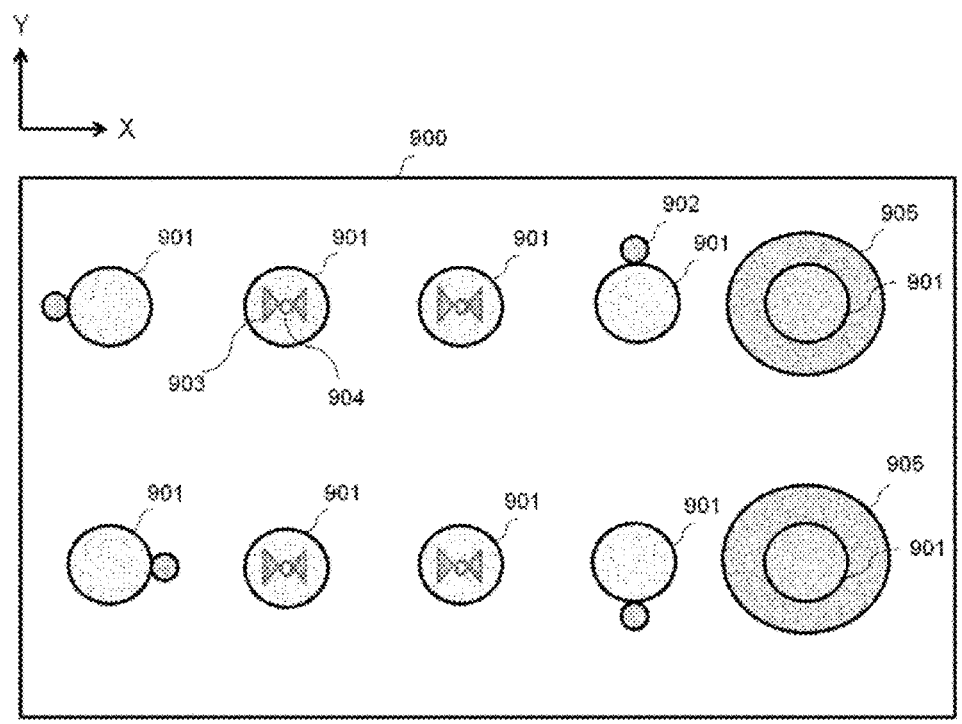

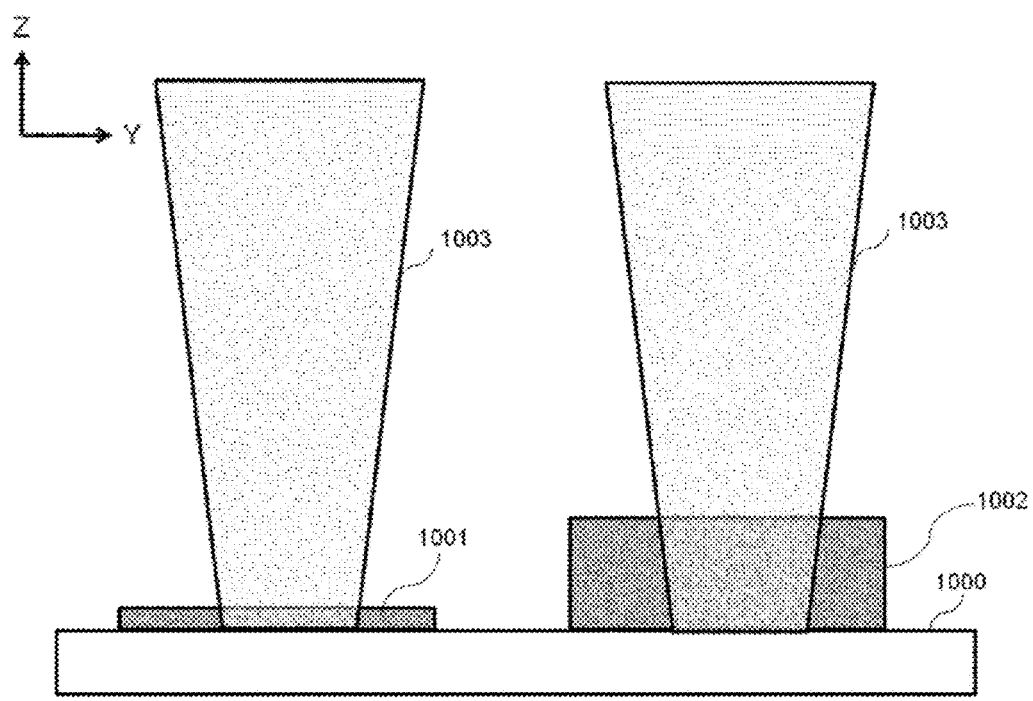
[Fig. 10]

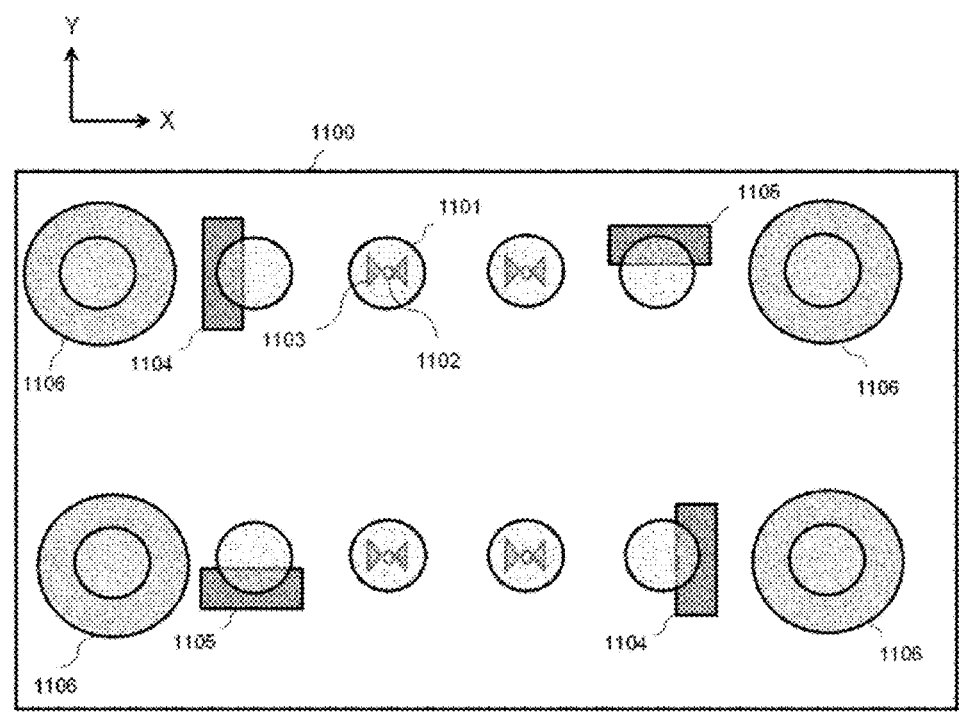
[Fig. 11]

[Fig. 12]
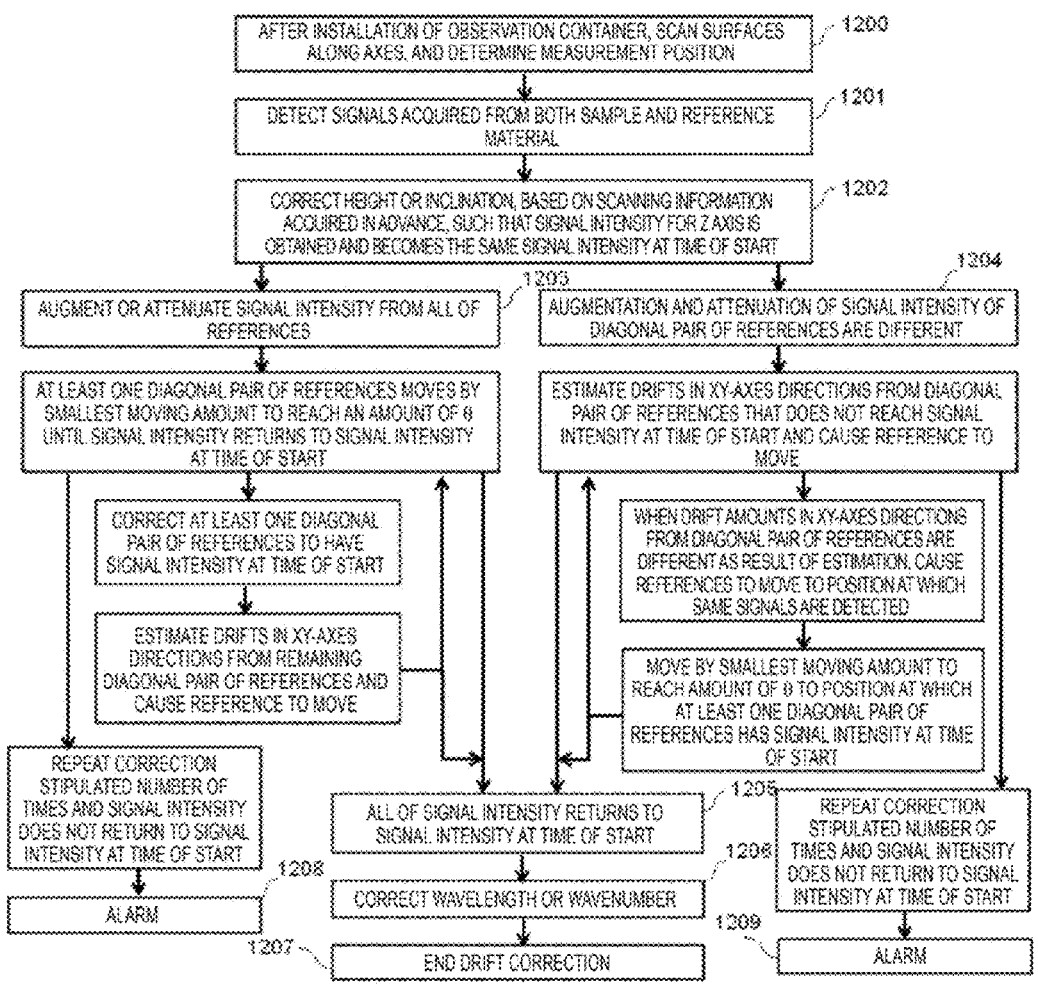

[Fig. 13]
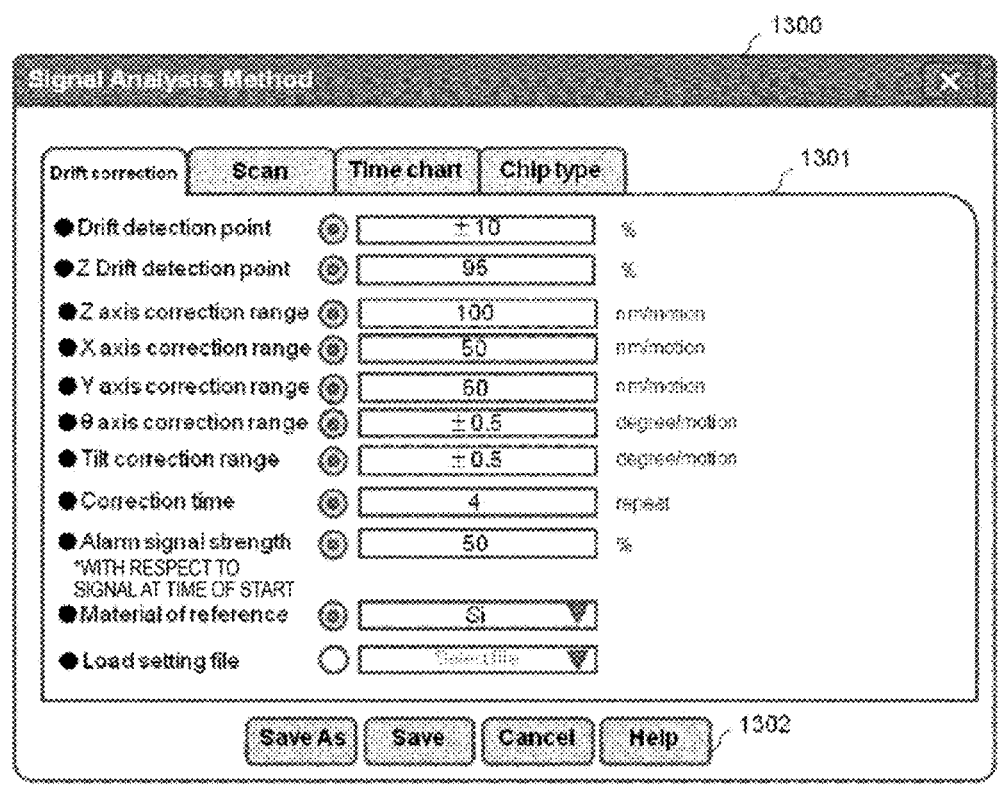

FIXED POSITION CONTROLLER AND METHOD

TECHNICAL FIELD

The present invention relates to fixed position control technology in biomolecule detection performed by using a Raman microscope.

BACKGROUND ART

Background art of this technical field includes PTL 1 that relates to a nanopore Raman DNA sequence. This publication discloses technology that causes biopolymers to approach a nanopore having an inner diameter of approximately 10 nm so as to increase excitation light with which the nanopore is irradiated and Raman scattered light of the biopolymers which pass through the nanopore, with the scattered light produced through conductive thin film provided in the vicinity of the nanopore, and then that detects the excitation light and scattered light and measures the biopolymers. Therefore, it is necessary to continuously hold a portion as an observation object at a fixed position with accuracy of tens to hundreds of nanometers, although a diameter of an irradiation spot of the excitation light is an important factor.

PTL 2 discloses another type of technology that relates to such fixed position control. In addition, PTL 3 discloses still another type of technology that detects and corrects a positional shift due to a temperature change.

CITATION LIST

Patent Literature

PTL 1: International Publication WO2012/043028A1
PTL 2: JP-A-62-43050
PTL 3: JP-A-2003-172684

SUMMARY OF INVENTION

Technical Problem

In the technology disclosed in PTL 1, the larger the diameter of the irradiation spot of the excitation light, the less an influence of a drift in the excitation light or adrift in the nanopore as a measurement portion. However, the large diameter of the irradiation spot has several demerits. First, since portions other than a measurement portion are irradiated, signals of noise and a background increase. Second, since the irradiation spot is large, much heat is supplied to the conductive thin film, service life of the conductive thin film is shortened, and thus it is not possible to measure for a long time. However, when the irradiation spot is small, the heat is likely to diffuse outside. Third, in a case where a plurality of nanopores are irradiated, the larger the irradiation spot, the higher an output is required from an excitation light source, and thus equipment needs to increase in size and costs. In other words, the closer the irradiation spot is to the size of the nanopore that the biopolymers approach or is to a size with which the biopolymers are detected, the more preferable. For this reason, it is necessary to control the excitation light and the nanopore at a fixed position with high accuracy. As a main factor of the drift, a change in an ambient temperature around an installed device is considered. It is easy to assume that a drift of a few micrometers or a few nanometers, as a drift within a range of a normal living environment, which varies depending on a configuration of the device or a temperature change, is produced due to a linear expansion coefficient of a material of which the device is configured. Hence, it is desirable to have a function of avoiding the drift.

In the technology disclosed in PTL 2, detection and measurement of a pattern in a determined region, in which a specific pattern is provided, are repeated, and thereby it is possible to perform the remeasurement at an optimal position by using a correction function even when the drift occurs; however, since the measurement is not performed during the detection of the pattern in the determined region, a data loss of sample measurement occurs during the detection of the pattern. For example, when pass of DNA occurs during the detection of the pattern causes the loss of data to an equivalent amount in a nanopore Raman DNA sequence. As a result, since an amount of data of the DNA sequence acquired per unit time decreases, it is necessary to prolong measurement time to an equivalent amount thereof. Further, in a case where the drift occurs during the pass of the DNA and detection of the pattern is performed for correction, it is possible to partially analyze data of the DNA which is acquired during the pass, and loss of characteristics of the nanopore Raman DNA sequence in which it is possible to analyze a single molecule is likely to occur. For example, when a correction operation is performed at a position at which 5,000 bases are measured during measurement of a DNA sequence having 10,000 bases, the remaining 5,000 bases pass through the nanopore during the correction, and thus it is not possible to perform the measurement. Even when a drift is detected before the correction and movement of DNA is stopped, there is likely to be a region in which it is not possible to perform measurement because the movement due to inertial motion is not rapidly stopped.

In recent years, studies on genome sequencing, an RNA analysis, an epigenome analysis or the like at a one-cell level are actively performed, and differences depending on cells or various types of changes occurring in a time change in the same cell are analyzed. Genome sequences in individuals are known to be different for each cell in some cases. In particular, when a cancer tissue is harvested and the genome sequence is analyzed, data of a mixture of normal cells and cancer cells is usually acquired. Since the cancer cells change with time, a plurality of types of mixed sequence data are acquired in some cases. When it is possible to determine the genome sequence of the cancer tissue for each cell, more accurate knowledge on causes and propagation of cancer is considered to be acquired, and thus studies thereon are performed day by day. For the purposes, a Raman nanopore DNA sequencer is useful in analysis of DNA of a single molecule in one cell.

In addition, in the technology disclosed in PTL 3, since a device is provided with various types of means such as displacement detecting means, vibration means, and heating and cooling means, which are not needed to achieve original objects of measurement, the device has a complicated configuration, and thus the device needs advance control and increases in costs. In order to reduce the influence of heating as a main factor of the drift, options of using invar or diamond which has a small linear expansion coefficient are provided for the entire device; however, it is not practical regarding cost or machinability. In addition, a method in which large heat capacity makes it difficult to receive influences of an ambient temperature is also provided as an option; however, a lack of convenience is caused in that an increase in weight due to the large heat capacity requires a broad site in which the device is installed, or it is necessary to prepare a strong desk or the like on which the device is installed.

Objects of the invention in the present application are to solve problems described above and to provide a fixed position controller in which it is possible to simultaneously observe the sample and perform fixed position control on a sample, and a fixed position control method.

Solution to Problem

In order to achieve the objects described, in the present invention, there is provided a fixed position controller including: an irradiation optical system that is capable of performing simultaneous irradiation with at least one or more beams of excitation light; a detector that detects a signal generated from an irradiation position through irradiation with the excitation light; a substrate that is provided with at least one nanopore and reference object; and a position control unit that calculates a position on a measurement sample which is irradiated with the excitation light, in response to the detection signal acquired from the reference object when the measurement sample positioned in the nanopore and the reference object are simultaneously irradiated with the excitation light, and that controls a fixed position of the irradiation on the measurement sample with the excitation light based on the calculation results. The measurement sample is measured while the position of the irradiation with the excitation light is controlled.

In addition, in order to achieve the objects described, in the present invention, there is provided a fixed position control method including: simultaneously irradiating at least one nanopore and at least one reference object in a substrate with excitation light; calculating a position on the measurement sample which is irradiated with the excitation light, based on a signal which is generated from the reference object; and measuring the measurement object, while controlling a position of the irradiation on the measurement sample with the excitation light, based on corresponding calculation results.

Advantageous Effects of Invention

According to the present invention, the measurement and the control of the fixed position are simultaneously performed, and thereby it is possible to perform analysis in a short time.

BRIEF DESCRIPTION OF DRAWINGS

FIG. 1 is a diagram showing an example of a configuration of a nanopore Raman DNA sequencer according to Example 1.

FIG. 2 is a diagram showing an example of a sectional configuration of a detecting unit and an observation container of the nanopore Raman DNA sequencer according to Example 1.

FIG. 3 is a diagram showing an example of a multi-nanopore substrate of a nanopore Raman DNA sequencer.

FIG. 4A is a diagram showing an example of the multi-nanopore substrate according to Example 1.

FIG. 4B is a diagram schematically showing an example of a configuration of irradiation with excitation light to the multi-nanopore substrate according to Example 1.

FIG. 5 is a graph showing a result obtained by scanning the excitation light for fixed position control according to Example 1.

FIG. 6 is a graph showing signal intensity obtained through repeating correction of fixed position control according to Example 1.

FIG. 7 is a diagram showing another example of a multi-nanopore substrate according to Example 2.

FIG. 8 is a graph showing a result obtained by scanning a silicon single crystal as a reference object in an X-axis direction according to Example 2.

FIG. 9 is a diagram showing another example of a multi-nanopore substrate according to Example 3.

FIG. 10 is a diagram showing an example in which reference objects having different heights are disposed on the multi-nanopore substrate according to Example 3.

FIG. 11 is a diagram showing another example of a multi-nanopore substrate according to Example 4.

FIG. 12 is a diagram showing an example of a flowchart of fixed position control according to Example 5.

FIG. 13 is a diagram showing an example of a screen display for setting, in advance, the fixed position control according to Example 5.

DESCRIPTION OF EMBODIMENTS

Hereinafter, various examples of the present invention will be described in order with reference to the figures.

Example 1

As Example 1, examples of a fixed position controller configured to include: an irradiation optical system that is capable of performing simultaneous irradiation with at least one or more beams of excitation light; a detector that detects a signal generated from an irradiation position through irradiation with the excitation light; a substrate that is provided with at least one nanopore and reference object; and a position control unit that calculates a position on a measurement sample which is irradiated with the excitation light, in response to the detection signal acquired from the reference object when the measurement sample positioned in the nanopore and the reference object are simultaneously irradiated with the excitation light, and that controls a fixed position of the irradiation on the measurement sample with the excitation light based on the calculation results, and a fixed position control method are described.

In the example, in the following description, a nanopore Raman DNA sequencer is provided as a model example of the fixed position controller that causes biopolymers as the measurement samples to approach the nanopore and detects a Raman spectrum. In other words, the sequencer is an example of a sequencer 100 that causes biopolymers to approach a nanopore having an inner diameter of approximately 10 nm so as to increase excitation light with which the nanopore is irradiated and Raman scattered light of the biopolymers which pass through the nanopore, with the scattered light produced through conductive thin film provided in the vicinity of the nanopore, and then that detects the Raman spectrum.

FIG. 1 shows an example of a configuration of the nanopore Raman DNA sequencer according to the example. Here, a configuration and an operation of the sequencer are described, on the basis of an example of a case where the sequencer is applied to observation of Raman light, with an upright microscope as a basic configuration. Note that the configuration of the sequencer is not limited to the basic configuration of the upright microscope, and a configuration, in which an inverted microscope is used as the basic configuration and it is possible to detect a signal of a sample through irradiation with light, may be employed.

In the same figure, a light source 101 performs irradiation, as excitation light, with external light having a wavelength with which it is possible to generate fluorescence or the Raman scattered light. Examples of the light source 101 known in the corresponding technical field include a semiconductor laser, a krypton (Kr) ion laser, a neodymium (Nd) ion laser, an argon (Ar) ion laser, a YAG laser, a nitrogen laser, a sapphire laser, or the like. In a case where a plurality of nanopores are irradiated with the external light from the light source 101 as the excitation light, a multi-irradiating mechanism 113 is used. There is no limitation on the multi-irradiating mechanism 113, and it is possible to use a microlens array, a diffraction grafting type beam splitter, or a liquid crystal on silicon (LCOS). As will be described below, according to the sequencer of the example, with the use of such configurations, the nanopore and the reference object are irradiated with a plurality of beams of the external lights as the excitation light. In addition, in order to irradiate a microscope observation container with the external light from light sources and to converge the light on the container, it is preferable to combine the light sources and to use a confocal lens and an objective lens 102. Optical systems described above from the light source 101 to the objective lens 102 are collectively referred to as an irradiation optical system.

A microscope observation container 103 is provided on an XY stage 104 and the XY stage 104 as positioning means is capable of adjusting a position of the microscope observation container on a horizontal plane. Regarding a position in a vertical direction, a Z-axis adjusting mechanism 105 adjusts a sample as a measurement object such that the sample is positioned in a region on which light focuses by the objective lens 102. The XY stage 104 may be provided with the Z-axis adjusting mechanism 105. Accurate adjustment may be performed by using a θ-axis stage or a gonio stage as the positioning means, in addition to the stage. A drive control part 115 controls the positioning means, and a user can operate the drive control part 115 by using a computer 116.

In addition, as illustrated in the same figure, as a configuration of the sequencer, a filter 106 such as a notch filter, a short pass filter, or a long pass filter, a beam splitter 107, a diffraction grafting 108, and the like may be combined, depending on a purpose of measuring a measurement wavelength region or the like. Otherwise, a mirror 112 or a pinhole, a lens 114, and a near-infrared (NIR) mirror 117 may be used according to necessity of arrangement of optical elements. In order to detect the fluorescence or the Raman scattered light, it is possible to select an appropriately preferable constituent elements.

As the detector that detects the signal generated from an irradiated position through the irradiation with the excitation light, it is possible to use any spectroscopic detector as long as the spectroscopic detector is a detector that is capable of detecting the fluorescence and the Raman scattered light. In addition, it is preferable that a detector 109 have a photomultiplier mechanism, such as an image intensifier, such that sensitivity is prevented from being reduced due to a high speed of the detection. Further, it is preferable that the detector 109 include a capacious memory in which it is possible to directly record image information of the Raman scattered light or the like, and an analyzer 118 in the sequencer 100 is capable of performing analysis at a high speed without a cable, a board, or a computer. Note that the analyzer 118 may be provided with a frame buffer memory in which measurement values from the detector 109 is recorded. In addition, the analyzer 118 may be configured to be connected to the computer 116 for performing digitalization or arithmetic processing on the measurement values from the detector 109 or the like, and outputting results.

Further, a nanopore Raman DNA sequencer 100 of the example may have a function of being capable of brightfield observation. For this purpose, as shown in FIG. 1, an LED 110 is used as an irradiation light source having a bright field, and a two-dimensional detector 111 is used as a bright-field imaging element. It is possible to use one or a plurality of one-dimensional or two-dimensional detector 111 according to the number and arrangement of the samples in the used microscope observation container. Examples of such a spectroscopic detector include a charge-coupled device (CCD) image sensor, a complementary metal-oxide-semiconductor (CMOS) image sensor, an image sensor of another high-sensitivity element (avalanche photodiode or the like), and the like.

<Description of Observation Container>

As shown in an example of a sectional configuration in FIG. 2, the microscope observation container 103 used in the sequencer 100 is formed of an observation container 201 in which a substrate 203 provided with at least one nanopore 202 and a reference object, which will be described below, is disposed. The observation container 201 is configured to have two closed spaces, that are, a sample introducing compartment 204 and a sample outlet compartment 205, which are separated with the substrate 203 having the nanopore 202. However, the sample introducing compartment 204 communicates with the sample outlet compartment 205 through the nanopore 202. The sample introducing compartment 204 and the sample outlet compartment 205 are filled with liquids 210 and 211 which are introduced via inlet paths 206 and 207 connected to both compartments, respectively. The liquids 210 and 211 flow out from outlet paths 208 and 209 connected to the sample introducing compartment 204 and the sample outlet compartment 205, respectively. The inlet path 206 and the inlet path 207 may also be provided at positions which face each other with the substrate 203 therebetween; however, the configuration is not limited thereto. The outlet path 208 and the outlet path 209 may also be provided at positions which face each other with the substrate 203 therebetween; however, the configuration is not limited thereto.

The substrate 203 is provided with a base, a conductive thin film 216 formed to face the base, and the nanopore 202 that is provided in the conductive thin film 216 and communicates with the sample introducing compartment 204 and the sample outlet compartment 205. The substrate is disposed between the sample introducing compartment 204 and the sample outlet compartment 205 of the observation container 201. In the figure, the reference object according to the example is omitted from the substrate 203.

In FIG. 2, reference sign 213 represents a sample that is observed, and reference signs 214 and 215 represent first and second electrodes. Voltage applying means (not shown) applies a voltage between the first electrode 214 provided in the sample introducing compartment 204 and the second electrode 115 provided in the sample outlet compartment 205. In addition, an ammeter may be disposed between the electrodes. Current between the first electrode 214 and the second electrode 215 may be appropriately determined in terms of determination of a passing speed of the sample through the nanopore, and, preferably, about 100 mV to 300 mV as long as the current is applied to DNA in a case where an ion liquid that does not contain the sample is used;

however, the current is not limited thereto. The electrodes can be manufactured of metal such as a platinum group such as platinum, palladium, rhodium, or ruthenium, gold, silver, copper, aluminum, or nickel; and graphite such as graphene (with any one of a single layer or multiple layers), tungsten, or tantalum.

Biomolecular polymers as the measurement samples that pass through the nanopore 202 through the voltage application between the electrodes generates the Raman light as the excitation light; however, it is possible to augment the Raman light with the conductive thin film 216 prepared in the vicinity of the nanopore 202 and caused to generate a near field. The conductive thin film 216 provided in the vicinity of the nanopore is formed to have a planar shape, as will be clear from definition of a thin film. The conductive thin film 216 has a thickness of 0.1 nm to 10 nm, and preferably 0.1 nm to 7 nm, depending on an employed material. The thinner the conductive thin film, the more it is possible to limit the near field that is generated and thus it is possible to perform analysis with high resolution and high sensitivity. In addition, there is no particular limitation on the size of the conductive thin film, and it is possible to appropriately select the size in accordance with sizes of the used substrate and the nanopore, a wavelength of the excitation light used, or the like.

According to the sequencer of the example, it is possible for the substrate 203 to be formed of a material of an electrical insulator, such as an inorganic material and an organic material (including a polymer material). Examples of materials of the electrical insulator that configure the substrate include silicon, a silicon compound, glass, quartz, polydimethylsiloxane (PDMS), polytetrafluoroethylene (PTFE), polystyrene, polypropylene, and the like. Examples of the silicon compound include silicon oxynitride such as silicon nitride, silicon oxide, and silicon carbide. In particular, it is possible to manufacture the base that configures a support of the substrate by using any material, and examples of the material include silicon or a silicon compound.

There is no particular limitation on the size and the thickness of the substrate 203 as long as it is possible to be provided with the nanopore 202. It is possible to manufacture the substrate through a method known in the corresponding technical field or it is possible to obtain the substrate as a commercially available product. For example, it is possible to manufacture the substrate by using technology of photolithography, electron-beam lithography, etching, laser ablation, injection molding, casting, molecular-beam epitaxy, chemical vapor deposition (CVD), dielectric breakdown, electron beams, or focused ion beams. The substrate may be coated so as to avoid non-targeted adsorption of molecules to a surface thereof.

<Description of Nanopore>

In the example, the "nanopore" and a "pore" are holes (opening) having a size of nanometers (nm) (that is, a diameter of 1 nm or larger and smaller than 1 μm), and mean holes which penetrate through the substrate and through which the sample introducing compartment communicates with the sample outlet compartment. The holes of the nanopore and the pore indicate opening circles of the nanopore and the pore in a portion in which the nanopore and the pore are in contact with a sample solution. During the analysis of the biopolymers, the biopolymers or ions in the sample solution approach the nanopore from one opening and flows out from the same opening or an opening on the opposite side to the outside of the nanopore. The substrate 203 used in the sequencer of the example is provided at least one nanopore 202, usually. The nanopore is specifically provided in the conductive thin film 216; however, the nanopore may also be simultaneously provided in an insulator as the base in some cases.

The conductive thin film 216, which is formed of a material and has the thickness that are suitable for the forming of the holes having the nanosize, is formed on the substrate 203, and thereby it is possible to provide the nanopore 202 in the substrate in a simplified and efficient manner. Regarding the forming of the nanopore, examples of the materials of the conductive thin film 216 include, preferably, silicon oxide (SiO2), silicon nitride (SiN), silicon oxynitride (SiON), metal oxide, metal silicate, or the like. In addition, the conductive thin film and the entire substrate in some cases may be substantially transparent. Here, "being substantially transparent" means that it is possible to transmit 50% or more of external light, and preferably, 80% or more thereof. In addition, the conductive thin film 216 may be a single layer or multiple layers. The conductive thin film 216 has the thickness of 1 nm to 200 nm, preferably, 1 nm to 50 nm, and, more preferably, 1 nm to 20 nm. It is possible to form the conductive thin film 216 on the substrate 203 through technology known in the corresponding technical field, such as low-pressure chemical vapor deposition (LP-CVD).

Further, it is preferable that an insulating layer be provided on the conductive thin film 216. Preferably, the insulating layer has a thickness of 5 nm to 50 nm. It is possible to use any material of the insulator in the insulating layer, and it is preferable to use, for example, silicon or a silicon compound (silicon nitride, silicon oxide, or the like).

As described above, it is possible to select an appropriate size of the hole size of the nanopore depending on a type of biopolymer as an analysis object. The nanopores may have a uniform diameter; however, the nanopores may have different diameters different depending on portions. The nanopore may be connected to a pore having a diameter of 1 μm or larger. The nanopores provided in the conductive thin film 216 of the substrate have the smallest diameter portion, that is, the smallest diameter of the corresponding nanopores is a diameter of 100 or smaller, for example, 1 nm to 100 nm, preferably, 1 nm to 50 nm, for example, 1 nm to 10 nm, specifically, 1 nm to 5 nm, and preferably, 3 nm to 5 nm.

A diameter of ssDNA (single-stranded DNA) as an example of a measurement sample 213 is about 1.5 nm, and an appropriate range of the diameter of the nanopore that is used for analysis of ssDNA is about 1.5 nm to 10 nm, and, preferably, about 1.5 nm to 2.5 nm. A diameter of dsDNA (double-stranded DNA) as another example is about 2.6 nm, and an appropriate range of the diameter of the nanopore that is used for analysis of dsDNA is about 3 nm to 10 nm, and, preferably, about 3 nm to 5 nm. Similarly in a case where other biopolymers such as proteins, polypeptides, or carbohydrates are the analysis objects as the sample, it is possible to select the diameter of the nanopore depending on a dimension of an outer diameter of the biopolymer.

It is possible to adjust a depth (length) of the nanopore by adjusting the thickness of the substrate 203 or the conductive thin film 216. It is preferable that the nanopore have the depth by monomer unit of which the biopolymer of the sample as the analysis object is formed. For example, in a case where nucleic acids are selected as the biopolymers, it is preferable that the nanopore have the depth of a size of three or more bases, for example, about 1 nm or larger. The nanopore basically has a circular shape; however, it is possible for the nanopore to have an elliptic shape or a polygonal shape.

It is possible for the substrate to be provided with at least one nanopore, and, in a case of a plurality of nanopores, the nanopores may be regularly arranged. It is possible to form the nanopore using nanolithography technology or ion beam lithography technology, through a method known in the corresponding technical field, such as, through irradiation with electron beams from a transmission electron microscope.

<Description of Conductive Thin Film>

When the conductive thin film 216 is not have a planar shape, but has a bent shape, the near field is induced in the bent portion, leak of light energy occurs, and the Raman scattered light is generated in a non-targeted portion. In other words, background light increases, and an S/N ratio decreases. Therefore, it is preferable that the conductive thin film 216 have the planar shape. In other words, it is preferable that the sectional shape not be the bent shape, but a straight-line shape. It is preferable that the conductive thin film be formed to have the planar shape in that it is not only effective to decrease in the background light and to increase the S/N ratio, but also in terms of uniformity of the thin film and reproducibility in manufacture of the thin film.

It is possible for the conductive thin film to have any shape as long as it is possible to generate the near field through the irradiation with the external light and to augment the field with the shape. A probe that generates such a near field is known in the corresponding technical field, and thus known examples thereof include a shape having a tip with an acute angle, a metal bow-tie structure, or the like, in which it is possible to generate and strengthen the near field through tip enhanced Raman scattering (TERS) and to have an augmentation field. The shape having the tip with the acute angle is described as an example of a preferable planar shape of the conductive thin film, and it is particularly preferable that the tip is provided on a surface of the nanopore. In this case, the angle of the tip is 10 to 80 degrees, preferably, 20 to 60 degrees, and, more preferably, 20 to 40 degrees. For example, regarding a preferable shape of the conductive thin film (light scatter) that forms near-field light, JP-A-2009-150899 is referred to. Note that the vertex portion of the tip of the conductive thin film may not strictly mean a point, but may be a rounded shape having a curvature radius which is smaller than or equal to a determined curvature radius, and preferably 10 nm or smaller. It is possible for the shape of the conductive thin film other than the tip with the acute angle to employ an angle which is more obtuse than that of the vertex of the tip. Here, since the near field is induced in a corner portion and leak of the light energy occurs, it is preferable to avoid having a complicated shape in portions other than the tip having the acute angle, which face the nanopore, and to employ a circular shape, a straight-line shape without a corner. In addition, it is possible for the entire shape of the conductive thin film to be any as long as the tip with the acute angle is provided in the shape, and it is possible for the shape to be polygons such as a triangle, a quadrangle, and a pentagon, a fan shape, a combination of a circle and a triangle.

On the other hand, it is possible to employ the metal bow-tie structure as the shape of the conductive thin film. In other words, two conductive thin films having a circular shape, an elliptic shape, or a polygonal shape are disposed such that projection portions of the shapes face each other. Regarding the metal bow-tie structure, for example, U.S. Pat. No. 6,649,894 is referred to. It is possible to consider the metal bow-tie structure as a structure in which a gap (opening) is inserted in the region in which the near field is formed. The insertion of the gap introduces anisotropy and the detection sensitivity is improved. Regarding the description of such technology, for example, U.S. Pat. No. 6,768,556 and U.S. Pat. No. 6,949,732 are referred to.

At least a part of the conductive thin film, or, particularly preferably, a structure of the tip or the like thereof that generates the near field is provided to face the nanopore. As long as at least a part of the conductive thin film, or, particularly preferably, the tip thereof is provided to face the nanopore, the conductive thin film may be disposed on a front surface of a solid substrate or may be disposed between the solid substrates. For example, it is possible to dispose the conductive thin film on the front surface of the solid substrate such that the conductive thin film faces the opening of the nanopore. Otherwise, it is possible to dispose the conductive thin film at a substantially intermediate position (depth) on the solid substrate in a central-axis direction of the nanopore. In this case, it is preferable that the conductive thin film have an interposed structure of being disposed between thin film portions of the solid substrate. In this manner, since the near field is formed in the vicinity of the intermediate portion of the nanopore in the central-axis direction (depth direction), it is possible to generate the Raman scattered light of the biopolymers in the nanopore while a shape and a moving speed of the biopolymers is controlled, and it is possible to perform the analysis with high accuracy and high sensitivity. Note that, in a case where the conductive thin film is disposed on the solid substrate, it is preferable that the conductive thin film be disposed in consideration of a polarizing direction of the external light with which the irradiation is performed.

In addition, at least one conductive thin film may be disposed for each nanopore, and an odd number of the conductive thin films or an even number of the conductive thin films may be provided. For example, it is possible to dispose one, two, three, four, or more conductive thin films for each nanopore. As will be described in Examples which will be described below, when a plurality of conductive thin films are provided, a field of intense light is formed. Therefore, it is preferable to dispose two or more conductive thin films for each nanopore. Otherwise, it is possible to form the conductive thin films as one thin film having a plurality of units, with the shape described above as one unit.

It is possible to form the conductive thin film of a material having the conductivity and light scattering properties. Examples of such materials include metal such as a platinum group such as platinum, palladium, rhodium, or ruthenium, gold, silver, copper, aluminum, or nickel; and graphite such as graphene (with any one of a single layer or multiple layers).

In a case where the plurality of conductive thin films are disposed, particularly, to be connected to each other, important points are as follows. In the case where the plurality of conductive thin films are disposed to be connected to each other, at least a part of the shape of the conductive thin film as a whole, which is obtained as a result of the connection to each other, or, particularly preferably, a shape of a portion thereof, which faces the nanopore, needs to have a tip with an acute angle. When the plurality of conductive thin films are connected in the vicinity of the nanopore, there is a concern that the tip with the acute angle will be lost. However, since the tip needs to efficiently form the near field, the loss has to be avoided. In this respect, in a case of using one conductive thin film, there is a concern that the same problem will arise when the conductive thin film is disposed to surround the entire circumference of the nanopore. In other words, charges induced in the conductive thin film due to the excitation light are likely to move around through the conductive thin film surrounding the entire circumference of the nanopore, and thus there is a concern that a problem will arise in that dipoles are not form in the nanopore portion. Therefore, in an analysis chip of characteristics of the biopolymers, it is preferable that at least one conductive thin film not be disposed over the entire circumference of the nanopore, but be disposed only over a part of the solid substrate in which the nanopore is formed.

It is preferable that the conductive thin film 216 be disposed such that the tip faces the opening of the nanopore. More specifically, the conductive thin film is disposed such that the tip of the thin film faces the opening of the nanopore within a surface orthogonal to the central axis of the nanopore. In addition, in a case where at least two conductive thin films are disposed, it is preferable that the conductive thin films be disposed to face each other with the opening of the nanopore therebetween. In such a case, the conductive thin films are irradiated with the external light, the conductive thin films causes the near field to be generated at the tip facing the nanopore, and causes the Raman scattered light to be generated from the biopolymers that approach the nanopore.

It is possible to manufacture the conductive thin film through a method known in the corresponding technical field and to dispose the conductive thin film on the solid substrate. For example, in a case where the conductive thin film is formed of silver, a silver thin film having a desirable thickness is formed on the substrate through sputtering, and then it is possible to form a desirable shape with the electron beam. In addition, in a case where the conductive thin film is formed of a single layer of graphene, it is possible to put, on a support substrate, the graphene manufactured from graphite, to perform irradiation with the electron beam, and to form the graphene having a desirable shape.

The analysis chip in the sequencer of the example is irradiated with the external light, thereby, the biopolymers approaching the nanopore are excited, the Raman scattered light is Generated, and thus it is possible to analyze the characteristics of the biopolymers, based on the spectrum of the Raman scattered light. Since the formed near field basically has the same thickness as the thickness of the conductive thin film, that is, the conductive thin film is orthogonal to the central axis of the nanopore, the thickness of the formed near field in the central-axis direction is substantially the same as the thickness of the conductive thin film. Therefore, the use of the analysis chip of the example enables the analysis of the biopolymers with high spatial resolution and high sensitivity.

<Description of Measurement Operation>

The liquid 210 shown in FIG. 2 is the sample solution that contains the sample 213 as the analysis object. It is preferable that the liquid 210 contain only an ionic liquid that contains, preferably, a large amount of ions as charge carriers, in addition to the samples 213. It is preferable that the ionic liquid be an aqueous solution in which electrolytes having a high ionization degree are dissolved, and it is possible to appropriately use, for example, a potassium chloride aqueous solution. It is preferable that the sample 213 have the charges in the ionic liquid. The samples 213 are typical biopolymers.

The voltage application to the electrodes 214 and 215 causes the charges and the samples 213 to pass through the nanopore 202 from the sample introducing compartment 204 and to move to the sample outlet compartment 205. When the samples 213 pass through the nanopore 202 irradiated with the excitation light, a Raman scattering spectrum augmented by the conductive thin film 216 is effectively collected as the Raman light with a liquid immersion medium 217, the Raman light reaches the detector 109 through an objective lens 218 corresponding to the objective lens 102 in FIG. 1, and the analysis is performed.

FIG. 3 shows an example of a configuration of a multi-nanopore substrate that is used, in general. As shown in the figure, a plurality of nanopores 302 and conductive thin films 303 are provided on a substrate 301. These correspond to the nanopores 202 and the conductive thin films 216 in FIG. 2. 20 nanopores 302 and conductive thin films 302 are provided in a grid shape; however, the arrangement is not limited thereto. The multi-irradiating mechanism 113 irradiates the nanopores 302 with the excitation light also in the multi-nanopore substrate 301, the detector 109 described in FIG. 2 performs the detection.

<Description of Measurement Using Reference Object>

A drift in the excitation light described above and a drift in the observation container occur due to a temperature change in a common environment around the installed sequencer, a temperature change with heat from a motor that drives the stage, or the like, and a desirable signal is not obtained in some cases when the nanopore is not correctly irradiated with the irradiation light. The nanopore Raman DNA sequencer 100 of the example uses a substrate provided with reference objects shown in FIG. 4A. A multi-nanopore substrate 401 in FIG. 4A is provided with reference materials 404, 405, and 406 as the reference object, in addition to a plurality of nanopores 402 and conductive thin films 403, and the use of the multi-nanopore substrate 401 enables the desirable signal to be acquired without an influence of an environmental change during the observation. The nanopores 402 and the conductive thin films 403 correspond to the nanopores 202 and the conductive thin films 216 in FIG. 2, respectively. The reference object on the multi-nanopore substrate means an object as a reference used for eliminating an influence of the drift due to the temperature change or the like described above.

In the sequencer of the example, for the first time, observation container 201 including the multi-nanopore substrate 401 is installed in the sequencer 100. As schematically shown in FIG. 4B, after the installation, the irradiation optical system of the multi-irradiating mechanism 113, the objective lens 218, and the like is used to match positions on the multi-nanopore substrate 401, which is irradiated with a plurality of beams of excitation light, positions of the nanopores 402. As means for matching the positions at an initial stage, various stages such as the XY stage 104 is driven while the irradiation with the excitation light is performed, and the Raman scattered light produced from the reference materials 405 and 406 as model examples of the reference objects or the nanopores 402 is detected. Therefore, it is necessary to perform designing and positional adjustment in advance such that the arrangement of the nanopores 402 and the reference materials 404 to 406 on the multi-nanopore substrate 401 matches the arrangement of the irradiation of the plurality of beams of excitation light. The detection is not limited to the Raman scattered light, and fluorescence may be detected with a fluorescent material as the reference materials 404 to 406. It is preferable to acquire sufficient signals in the detection. For example, it is possible to obtain the reference material as a commercially available product, and it is possible to perform the detection by fixing, to the multi-nanopore substrate 401, beads that produce the fluorescence.

Note that signal detection used in the position matching at the initial stage may be performed not only with the reference materials 404 to 406 as the reference object, but also with the signal acquired from the multiple nanopores and the conductive thin films. At this initial stage, the samples as the observation objects are not mixed in the solution, the solution, with which the observation container 201 is filled, has the Raman scattered light, and it is possible to acquire the signal augmented through the conductive thin film, similar to the samples. Therefore, it is possible to perform the position matching at the initial stage with high accuracy by using the signal.

In addition, by using the photolithography technology and the micro-processing, structures of silicon single crystals may be formed as the reference objects on the substrate, and the Raman scattered light of the silicon single crystals may be detected. A substrate, on which a flat single-crystal thin film is bonded, is also commercially available in general, and it is also possible to manufacture substrates having a stipulated thickness (that is, a height of the structure). In addition, as long as, without limitation to silicon, a material such as a single crystal having a stipulated crystal orientation plane or, without limitation to the single crystal, a flat and homogeneous material, of which an absolute value of the Raman scattering intensity is obtained with good reproducibility, forms a film or is bonded, then patterning using the photolithography technology is performed from the top thereof, and the materials are processed to form the structure as the reference object through the micro-processing, it is possible to use the structure not only in the positional adjustment, but also as intensity reference of the Raman scattered light. By using relative positioning means which is the same as means used during the forming of the nanopores, for example, arrangement marks for forming the structure, or a collective forming method in which it is not necessary to arrange a plurality of layouts, it is possible to form a layout pattern for arranging, as the reference object, the structure having the stipulated positions and Raman scattering intensity. Therefore, it is possible to arrange the nanopores and the reference objects on the multi-nanopore substrate with high accuracy.

Further, even in a case where the material at the positions, at which the nanopores 402 are formed, and the materials of the reference materials 404 to 406 as reference objects are different, the multi-nanopore substrate 401 is provided with a region in which the different materials face each other, it is possible to manufacture the substrate on which the arrangement of the structures related to the function of the nanopores and the reference objects as the structures of different materials, which have the stipulated positions and Raman scattering intensity, as long as a mask for microprocessing is formed through the lithography technology and the processing is performed. Here, the silicon single crystal is described as an example; however, the material is not limited thereto. Any material may be used as long as a spectrum having a peak within a wavenumber range, in which the detection needs to be performed, is applied to the material. For example, materials, with which it is possible to form a film or to perform the processing on the substrate, such as molybdenum oxide, tungsten oxide, aluminum oxide, zinc oxide, tin oxide, titanium oxide, or silicon carbide, may be selected.

As described above, means for preparing the reference objects by using the photolithography technology and the micro-processing is described; however, the means is not limited thereto. A case where it is difficult to perform the processing according to the materials is assumed. For example, a film of a material of the reference material may be formed on a surface of the substrate, then the reference material may be covered with a material with which it is easy to perform the processing, a covered portion may be exposed through etching or the like to have only a size and a range by which a signal is acquired, and the fluorescence or the Raman light may be detected from the exposed portion.

In a configuration of the example, FIG. 5 shows a result obtained by using the silicon single crystal as an example of the reference object for matching the positions, and scanning the reference object in XY-axes directions by using the drive control part 115 that functions as a part of a position control unit. At this time, the axis, along which the scanning is performed, is not limited to the XY directions using the XY stage 104, and the scanning may be performed in a Z-axis direction using the Z-axis adjusting mechanism 105, and further the scanning may be performed in an inclined direction using a gonio stage or in a θ-axis direction. One surface is not only scanned along the XY axes, but also the method of the scanning is not limited. Movement to a coordinate position, at which the strongest signal is acquired, is performed in response to results of movement of the axes and operations of detecting signals through the irradiation, it is possible to start measurement from the coordinate axis at which the strongest signal is acquired.

Preferably, the measurement is started at the position after the scanning and desirable signal is acquired on the same coordinate axis until the measurement is completed; however, as described above, the drift occurs in a range of micrometers or nanometers due to dissipation of heat from the detector or the stage motor of the XY stage 104 or the like that configures the sequencer and the temperature change in the environment. In the sequencer of the example, while the signals from the nanopores 402 are detected on the start of the measurement of the liquid 210 in which the samples are started to be mixed, the drive control part 115 also functioning as a part of the position control unit performs the scanning operation on the reference materials 404 to 406 as the reference objects, and the computer 116 functioning as a part of the position control unit, or the analyzer 118 calculates a coordinate axis from which the strongest signal is released after the scanning, using the detection signals of the detector 109. Rescanning is performed around the coordinate axis from which the strongest signal intensity is released, under control by the drive control part 115 functioning as a part of the position control unit. At this time, in response to the result of the coordinate axis and the signal shown in FIG. 5 in which the range, in which the scanning is performed, is obtained at the time of initial positioning, control is performed such that the scanning is performed in a range in which the minimum required signal is acquired. This operation enables the fixed position control to be performed such that the minimum required detection signal is normally acquired.

In other words, the position control unit including the drive control part 115, the computer 116, or the like scans the spot positions with the excitation light with respect to the measurement samples and the reference objects, calculates the position at which the measurement sample is strongly irradiated with the excitation light, based on the signals acquired from the reference object, and controls the spot position on the measurement sample at a desirable position in response to the calculation result.

Note that, when the signal from the nanopore is assumed to be used as the signal for positional control during the measurement of the sample using the liquid in which the sample is mixed, detection of combination of, as the signal, a signal of the liquid itself as a solvent, and a signal of the samples as the observation objects passing the nanopore occasionally, that is, the biopolymers, is likely to be performed. Since the detection is a cause of an error, in the sequencer of the example, the position control unit performs the scanning of the fixed position control using only a detection signal from the reference material as the reference object during the measurement of the sample.

The range of scanning for the fixed position control during the measurement of the sample may be determined by using the results of the coordinate axis and the signal obtained by scanning the nanopore or the reference material which is examined in advance such as before shipment of the product. Preferably, information acquired from the reference material used during the position matching of the substrate at the initial stage immediately before the start of the measurement is used, and, more preferably, information acquired from the position of the nanopore during the position matching at the initial stage is used. It is desirable to determine the range in which the minimum required signal is acquired.

The scanning may be repeated at time intervals at which the scanning is performed during the measurement of the sample using the position control unit all the time; however, the scanning may be performed at regular intervals. Using the sequencer of the example, FIG. 6 shows an example of the signal intensity of the sample which is acquired by simultaneously performing the scanning on a cylindrical silicon single crystal as the reference object having a diameter of 700 nm and a height of 220 nm at a two-minute interval, performing the measurement of the Raman light, and repeating the correction based on the scanning result. The measurement was performed in conditions under which heat is generated in the motor or the like immediately after the start of sequencer and the drift in the temperature is likely to occur. Temperature in the sequencer was measured at the same time; however, even when the temperature change occurs as shown in the figure, the signal having the intensity of 80% or higher was verified to be maintained all the time when the intensity of the signal at the time of the start of the measurement was defined as 100%. On the other hand, when the measurement of the Raman light was performed immediately after the start of the sequencer, without performing the correction operation of the fixed position control of the example, the signal intensity decreased to 80% or lower after about five minutes, and a reduction of the signal was observed as time elapsed after the start, as shown in FIG. 6.

In addition, the interval at which the scanning for the fixed position control by the position control unit of the drive control part 115 or the like is not limited to a determined time interval. For example, a temperature sensor may be provided inside or outside the sequencer 100 or at a heat dissipation portion, the scanning operation for the fixed position control by the position control unit described above may be performed when a temperature change occurs per time or when the temperature sensor detects a temperature out of a determined range. In other words, the position control unit detects a predetermined temperature change, then starts to scan the spot position of the excitation light for the fixed position control, and controls the spot position at the desirable position.

In addition, as a method of driving the stage that performs the scanning by the position control unit described above, the one surface may be completely scanned along the XY axes; however, scanning along only the X axis of the start point of the measurement is performed in a required range described above, movement is performed along the X coordinate axis on which the strongest signal intensity is obtained, subsequently, the operation to perform the scanning along only the Y axis in the required range described above is repeated, and thereby the scanning time may be shortened. At this time, similar to the position matching, the stage drive axis, along which the scanning is performed, is not limited to XY, and the scanning may be performed in the Z-axis direction, in a θ-axis direction, or in an inclined direction using the gonio stage.

Through the operation of the fixed position control of the example described above, the positions on the substrate which are irradiated with the plurality of beams of excitation light and the positions of the multiple nanopores are controlled, and thus it is possible to acquire the minimum required signal from the multiple nanopores all the time.

Note that the acquired signal has the specific spectrum of the substance because the signal is the Raman light or the fluorescence. For example, a spectrum having the peak at $520\ cm^{-1}$ is acquired from the silicon single crystal. A drift (positional shift) of the detector itself may be corrected using the specific spectrum of the substance. In other words, it is possible to correct a position of the detector or information of an image element of the detector, using the spectrum of the reference material as the reference object. For example, in a case where the detector 109 has a drift, the detection is not performed by a predetermined image element on a position at which $520\ cm^{-1}$ of the Raman light of the silicon single crystal as the reference object is detected, for example, on a two-dimensional detection surface, but is performed by an image element at the drifted position, for example at a position at which $540\ cm^{-1}$ of the Raman light is detected. In other words, the sample does not obtain the peak at a position with a wavenumber at which the sample obtains the peak before, and the peak is detected at a position with a wavenumber different from the wavenumber above, or is detected as a weak peak.

However, since it is obvious that the silicon single crystal is used as the reference material, it is possible to correct the drift described above based on the peak of the reference material which is obtained as the drift using the detection signals of the image elements of the detector. At the time of measurement start, the detector may store the positions, at which the signal of the reference material is obtained, as information of a predetermined image element, a drift amount may be calculated from a position at which the signal of the reference material, which is obtained from an image element at the drifted position, and correction of the drift may be performed by a drifted distance using a driving mechanism (not illustrated) provided in the detector 109. Correction means is not limited to the driving mechanism, and other means may be used.

As illustrated in FIG. 4, in the sequencer of the example, the plurality of reference materials 404 to 406 are prepared at the end of the arrayed nanopores 402. As a result, the peaks of signals of the reference materials, which are obtained as a plurality of points by the detector 109, are used, and information of the positions of the image elements, in which the peaks are contained, and the wavenumber information are recalculated and corrected. Hence, since it is possible to perform the correction with high accuracy by using the materials in which the plurality of peaks are obtained, such materials may be used as the reference material. Here, an example of using the Raman light of the silicon single crystal is described; however, the configuration is not limited thereto, and another material that produces the Raman light or the fluorescence of the fluorescent material may be used.

According to the configuration of the example described above, it is possible to control the irradiation position of the excitation light to the fixed position without preparing a new driving mechanism that controls the environmental temperature or the temperature in the sequencer with high accuracy. In addition, it is possible to control the irradiation position to the fixed position without preparing a new mechanism that detects a shift of a position. Further, it is possible to control the detector itself to the fixed position without preparing a new mechanism in the detector, by using the at least one or more reference materials. In other words, according to the example, the reference materials as the reference objects are disposed on the substrate in which the nanopores are formed, and thereby it is possible to control, to the fixed position, the irradiation position with the excitation light in the nanopore Raman DNA sequencer, and to perform the signal detection with high accuracy.

Example 2

Example 2 is an example of the sequencer that reduces attenuation in the signal and is capable of scanning for the fixed position control. FIG. 7 shows an example of a configurational diagram of a multi-nanopore substrate 701 provided with reference materials 704, 705, and 706 of which the attenuation of the signals is further reduced, in the example. The multi-nanopore substrate 701 of the example also causes the biopolymers as the samples to pass through the nanopores and detects the biopolymers by using the nanopore Raman DNA sequencer shown in FIG. 1, similar to Example 1. At this time, in the example, when the excitation light, with which nanopores 702 and a conductive thin film 703 are irradiated by using the irradiation optical system shown in FIG. 4B, has the same spot diameter as the spot diameter of the excitation light with which the reference object is simultaneously irradiated, the reference materials 704 to 706 having a diameter which is smaller than the diameter of the sample at the nanopore position are disposed. In this manner, it is possible to effectively reduce the attenuation of the signal and it is possible to perform the scanning with the excitation light for the fixed position control. In addition, when the spot diameter of the excitation light is smaller than the diameters of the sample and the reference material, the spot diameter of the excitation light to the reference material is larger than the spot diameter of the excitation light to the measurement sample.

FIG. 8 shows, as an example, a detection result of a signal obtained from the scanning in the X-axis direction including a center position of two types of cylindrical silicon single crystals having diameters of 700 nm and 150 nm and a height of 220 nm. As shown in the same figure, when the silicon single crystal is shifted from the center position, the cylindrical silicon single crystal having the smaller diameter has remarkably large attenuation of the signal. For example, when the diameter of the sample that is irradiated with the excitation light at the nanopore position, that is, the diameter of an augmented field, is 700 nm, the attenuation of the signal from the reference material is remarkable, when the silicon single crystal having the diameter of 150 nm is used as the reference material. Therefore, it is possible to reduce the attenuation of the signal of the sample and to perform the scanning. Since the attenuation of the signal from the reference material side having the small diameter is remarkable, compared to a case where a loss in the signal of the sample is likely to occur with too broad a range of the scanning, it is possible to detect a desirable position even when the range of the scanning of the excitation light is narrow, and thereby it is possible to detect attenuation of the signal of the reference material without a loss of the signal of the sample, and to detect the desirable position with accuracy. The silicon single crystal is described as an example; however, the material is not limited thereto, and any material may be used as long as a spectrum having a peak within a wavenumber range, which needs to be detected, is applied to the material. For example, materials, with which it is possible to form a film or to perform the processing on the substrate, such as molybdenum oxide, tungsten oxide, aluminum oxide, zinc oxide, tin oxide, titanium oxide, or silicon carbide, may be selected. In addition, the same is true of use of the fluorescent material.

The method, in which the attenuation of the signal is reduced by reducing the diameter of the reference material with respect to the measurement sample, is described; however, the method is not limited thereto. It is preferable that the spot diameter of the irradiation to the reference material is smaller than the spot diameter of irradiation of the excitation light with which the sample is irradiated. In other words, it is also possible to irradiate the reference material with the excitation light having the spot diameter which is smaller than the spot diameter of the excitation light with which the measurement sample is irradiated. In general, the spot of the irradiation with the excitation light is reduced to be narrow using a lens or the like; however, in order not to make the irradiation spot have a size that is smaller than or equal to the wavelength, in principle, a part of the irradiation optical system shown as an example in FIG. 4B is modified, the irradiation spot is reduced by irradiating the reference material with the excitation light having a wavelength which is shorter than the wavelength with which the sample is irradiated, and it is possible to significantly augment and attenuate the signal from the reference material when the drift occurs, and to have a configuration in which the drift is detected with high sensitivity. In other words, it is also possible to use the excitation light having the wavelength which is shorter than that of the measurement sample, and to irradiate the reference material with the excitation light having the spot diameter which is smaller than the spot diameter of the sample.

In addition, in general, a pinhole or an aperture provided on the optical axis increases, and a depth of field increases. With this phenomenon, when the pinhole provided on the optical axis of the reference material decreases with respect to the pinhole provided on the optical axis of the sample, it is possible to detect the drift with high sensitivity since the augmentation and attenuation of the signal are remarkable with respect to the drift in a direction (Z-axis direction in FIGS. 1 and 4) perpendicular to the optical axis of the reference material.

According to the configuration in which the diameter of the reference object of the example is smaller than the diameter of the sample at the nanopore position, it is possible to detect the drift with higher sensitivity and to perform the fixed position control with high accuracy.

Example 3

Example 3 is an example of the sequencer that reduces attenuation in the signal and is capable of performing the fixed position control with high accuracy. In Examples 1 and 2, the configuration, in which the direction of the drift is detected through the scanning of the excitation light for the fixed position control even when the drift occurs due to the temperature change or the like in the sequencer, and correction in the drift direction reduces the attenuation of the signal, is described. In the example, without detecting the direction of the drift through the scanning, the drift direction and the drift amount are calculated and corrected, using the signal change obtained when the irradiation positions with the plurality of beams of excitation light and the positions of the nanopores and the reference objects are shifted.

FIG. 9 is a plan view showing an example of a multi-nanopore substrate 900 provided with reference materials 902 and 905 as the reference objects in the example. Similar to Examples 1 and 2, the biopolymers as the samples are caused to pass through a plurality of nanopores 904 and the detection of the biopolymers in the nanopores 904 is performed by using the nanopore Raman DNA sequencer 100 shown in FIG. 1. Similar to Example 1, in the example, the observation container 201 including the multi-nanopore substrate 900 is also installed in the sequencer. By using the irradiation optical system or the like shown as an example in FIG. 4B, after the installation, positions 901 on the multi-nanopore substrate 900, which is simultaneously irradiated with the plurality of beams of excitation light matches positions of the multiple nanopores 904. As means for matching the positions, various axes of and various types of stages 104 are driven while the multi-nanopore substrate 900 is irradiated with the excitation light, and the Raman scattered light produced from the reference material 902 is detected, and the signal intensity of the Raman scattered light and the information of the stage positions are stored in a storage medium of the computer 116, the analyzer 118, or the like. For this reason, also in the example, it is necessary to perform designing and positional adjustment in advance such that the arrangement of the nanopores on the multi-nanopore substrate 900 matches the arrangement of the irradiation of the plurality of beams of excitation light. The detection is not limited to the Raman scattered light, and fluorescence may be detected with fluorescent material as the reference material.

In the example, the irradiation spots 901 match the positions at which the maximum signals obtained from the nanopores 904 in the multi-nanopore substrate 900, and the reference material 902 is disposed at the position shifted from positions at which the maximum signals are generated. The reference material 902 may be disposed at the position shifted from the irradiation spot in advance. In addition, a position of the irradiation spot may be shifted to the reference material 902. The drifted direction, in which the shift occurs, is recognized, based on an increase in the signal in a case where the reference material 902 of four reference materials shown in the same figure is disposed at the position shifted in the Y-axis direction, and is shifted in the Y-axis direction, and the positional information of the image element of the detector 109 that detects the signals. Further, the drift amount is calculated, based on a relationship between the stage position information and the signal intensity of the result of the scanning operation performed during the initial position matching and an increase in the intensity of the signal generated when the reference material 902 is drifted. It is possible to perform correction operations by the stage driving to the position at which the strongest signal is acquired from the nanopore, based on the calculated drift direction and drift amount. At this time, three other reference materials are disposed at positions (vectors) which are different from the reference material 902, and thereby it is possible to correct the drifts in directions with high accuracy.

In the configuration of the arrangement in FIG. 9, a width, in which the position of the reference material is shifted, is determined by the detected drift amount, which needs to be detected. In a case of performing the detection with high accuracy, for example, the silicon single crystal is used as the reference material with reference to the scanning result shown in FIG. 8, it is possible to estimate the drift amount, based on the augmentation and attenuation of the signal detected when the silicon single crystal having the diameter of 150 nm is disposed at a position shifted from the center position, for example, by 200 nm.

FIG. 10 is a diagram of an example in which reference materials 1001 and 1002 as the reference object are disposed on a multi-nanopore substrate 1000 such that a drift in a Z-axis direction is detected in the sequencer of the example. The reference materials 1001 and 1002 correspond to the two reference materials 905 shown in the plan view in FIG. 9. For example, when the multiple nanopores 904 prepares the height of the reference material 1001 having the same height as a height of the position at which the strongest signal is detected, the reference material 1002 is disposed at a position higher than the reference material 1001, that is, have the height. As a result, in a case where the sample detected in the Z-axis direction is drifted in a rising direction, the signal from the reference material 1001 decreases, and the signal from the reference material 1002 increases. On the other hand, the signals from the reference materials 1001 and 1002 decrease in the case where the sample is drifted in a lowering direction. Here, it is preferable that the reference materials 1001 and 1002 have a diameter with a broad size in a degree, in which no influence is applied on the signal intensity, even when the drift occurs in the XY-axes directions. In this manner, it is possible to recognize and correct the drift direction of the Z axis with the augmentation and the attenuation of the signal of the reference materials.

The positions, at which the reference materials are positioned, are not limited to the arrangement described above. For example, the reference material 1002 may be disposed at a position which is lower than the reference material 1001. In addition, both reference materials and the multiple nanopores 904 are not prepared to have the same height as the position at which the signal most increases, one reference material is disposed at a position which is lower than the position of the nanopore 904 at which the signal most increases, and one reference material may be disposed at a position which is higher than the position of the multiple nanopores 904 at which the signal most increases. In other words, the reference materials 1001 and 1002, which are disposed to be shifted in the axial directions, are disposed at positions at which at least the drift amount on the Z axis can be detected, which need to be detected.

The silicon single crystal is described as the reference object and as an example; however, the material is not limited thereto, and any material may be used as long as a spectrum having a peak within a wavenumber range, which needs to be detected, is applied to the material. For example, materials, with which it is possible to forma film or to perform the processing on the substrate, such as molybdenum oxide, tungsten oxide, aluminum oxide, zinc oxide, tin oxide, titanium oxide, or silicon carbide, may be selected. In addition, the same is true of use of the fluorescent material.

Example 4

Example 4 is an example of another configuration in which the drift direction and the drift amount are calculated and corrected, using the signal change obtained when the irradiation positions of the excitation light and the positions of the nanopores are shifted. As another configuration in which the drift direction and the drift amount are calculated and corrected, in the example, unlike the configuration of the multi-nanopore substrate 900 shown in FIG. 9 the reference material is disposed at a position shifted in the drift direction which needs to be detected, with respect to the irradiation spot position and the signal changes in response to the drift, as shown in FIG. 11.

In the example, a configuration of a multi-nanopore substrate 1100 shown in FIG. 11 is used. Similar to Examples 1 to 3, the biopolymers as the samples are caused to pass through a plurality of nanopores 1102 arranged and the detection of the biopolymers in the nanopores 1102 is performed by using the nanopore Raman DNA sequencer. In the example, for the first time, the observation container 201 including the multi-nanopore substrate 1100 is installed in the sequencer 100. After the installation, positions 1101 on the substrate 1100, which is irradiated with the plurality of beams of excitation light are caused to match positions of the multiple nanopores 1102. As means for matching the positions, various axes of and various types of stages are driven while the multi-nanopore substrate 1100 is irradiated with the excitation light, and the Raman scattered light produced from the reference material is detected, and the signal intensity of the Raman scattered light and the information of the stage positions are stored in the computer 116, the analyzer 118, or the like. For this reason, it is necessary to perform designing and positional adjustment in advance such that the arrangement of the nanopores 1102 on the multi-nanopore substrate 1100 matches the arrangement of the irradiation of the plurality of beams of excitation light. The detection is not limited to the Raman scattered light, and fluorescence may be detected with the fluorescent material as the reference material.

The irradiation spots 1101 match the positions at which the maximum signals obtained from the nanopores 1102 in the multi-nanopore substrate 1100 in FIG. 11. The reference material 1104 and 1105 are disposed at positions at which the maximum signal is generated, and at positions shifted from the center of the irradiation spot. For example, the center of the rectangular parallelepiped reference material 1104 is shifted in the X-axis direction with respect to the center of the irradiation spot, and the reference material has a long side in the Y-axis direction. The center of the rectangular parallelepiped reference material 1105 is shifted in the Y-axis direction with respect to the irradiation spot, and the reference material is a rectangular parallelepiped having a long side in the X-axis direction. The direction, in which the drift occurs, is recognized, based on the augmentation and the attenuation in the signal in a case where the reference material 1104 is disposed at the position shifted in the Y-axis direction and is shifted in the X direction side, the augmentation and the attenuation in the signal in a case where the reference material 1105 is disposed at the position shifted in the X-axis direction and is shifted in the Y-axis direction, and the positional information of the image element of the detector 109 that detects the signals. Further, it is preferable that at least two or more rectangular parallelepiped reference materials 1104 and 1105 having the long sides in the Y-axis and X-axis directions, respectively, be installed. More preferably, when the drift in a rotating direction occurs if the reference materials are disposed on the outer side from the nanopores 1103 as the detection positions, the reference material on the outer side from the nanopores on the inner side is largely drifted. Therefore, it is possible to correct, with accuracy, the irradiation of the nanopore 1102 positioned on the inner side by performing the correction on the reference materials 1104 and 1105 on the outer side.

Reference materials 1106 have a height and thickness similar to those of the reference material 905 shown in Example 3 in which the reference materials are provided to have different heights in the Z-axis direction. The reference material is disposed at a position shifted from the irradiation spot in the perpendicular direction in advance, and the drift in the Z-axis direction is detected with the augmentation and the attenuation in the signal. Further, with the plurality of reference materials 1106, an inclination of the measured substrate 1100 may be detected. For example, the reference materials 1106 are disposed at four corners as shown in FIG. 11, an orientation of the inclination may be detected with the augmentation and the attenuation in the four signals, and correction for maintaining the flat surface may be performed with a stage for adjusting the inclination or the driving mechanism.

According to the example, it is possible to detect the rotating direction, as well as the drifts in the XYZ-axes directions. For example, as illustrated in FIG. 11, the rectangular parallelepiped reference material 1105 is disposed on both ends of the substrate. The center of the reference material 1105 is shifted in the Y-axis direction with respect to the center of the irradiation spot, and it is possible to detect the drift in the rotating direction with the long side thereof disposed in the X-axis direction. In a case where the substrate is drifted in a clockwise direction, the signals acquired from the two reference materials 1105 are simultaneously attenuated. In this phenomenon, the clockwise drift of the substrate is detected, and correction is performed by rotating the stage in a counterclockwise direction. In a case where the substrate is drifted in a counterclockwise direction, the signals acquired from the two reference materials 1105 are simultaneously augmented. In this phenomenon, the counterclockwise drift of the substrate is detected, and correction is performed by rotating the stage in a clockwise direction.

In the example, similar to configuration of Example 3, not only it is possible to calculate and correct the drift direction and the drift amount, but also it is possible to detect and correct the drift in the rotating direction.

Example 5

In Examples 1 to 4 described above, the correcting operations of the drifts on the axes are described; however, a rotating axis of a θ stage used in the correction is different from a rotating center of the rotating axis when the drift occurs. In a case where the drift in the rotating direction and the drift in the XYZ-axes direction of the reference material are combined, it is necessary to use the computer 116 or the analyzer 118, and to perform various types of drift corrections in order, based on the information of the signals acquired from the reference object. As Example 5, an example of the sequencer that is capable of performing appropriate drift correction in such a case is shown.

FIG. 12 shows a flowchart of an example of the drift correction in the example. First, the observation container 201 including the substrate 1100 shown in FIG. 11 is installed in the sequencer 100. After the installation, the observation container 201 is irradiated with the excitation light, and the measurement position at which a scanning operation is performed to search a position, at which the strongest signal intensity of the nanopores 1102 is detected, is determined (1200). Simultaneously, the signal intensity and the positional information are acquired from the reference materials 1104, 1105, and 1106, and are stored in the storage medium of the computer 116, the analyzer 118, or the like (1201).

After the scanning, the nanopore moves to the position at which the strongest signal intensity is detected, the signal of the biomolecules that pass through the nanopore, and, at the same time, the signal measurement is started from the reference material. The signals from the reference material during the measurement start are stored in order, and then is used during the drift correction.

In a case where the drift occurs due to the temperature change after the measurement start, the drift is detected with the change in reference values since a change in the signal of the reference values is found. The detection and the calculation may be performed all the time, or in order to reduce the calculation process, as described above, for example, reference values of signals are regularly acquired, such as acquisition of data at 10-minute interval, and the drift may be detected. Note that the signal intensity for detecting the drift may be set in advance.

FIG. 13 shows a configurational example of condition setting of the drift detection and correction in the sequencer of the example. The display screen 1300 is a screen that is displayed on a display or the like of the computer 116 or the analyzer 118. An item represented by "drift detection point" in a drift correction window 1301 in a display screen 1300 is an item that sets a value by which the drift is recognized when the value is smaller than, for example, 90% of a signal value acquired from the reference material during the start. When the drift is detected, first, the signal of the reference material 1106 for detecting the drift on the Z axis is detected, and correction is performed such that the reference material has the height and the inclination and acquires the same signal intensity as that during the start, based on the scanning information acquired in advance (1202). This is a process of checking whether a signal value changes from another reference value, simply due to the shift on the Z axis and the shift of focus, and the drift is not recognized. Therefore, a value, by which the signal intensity from a Z-axis reference material is recognized as the drift, for example, may be set to 95% as "Z drift detection point" as shown in FIG. 13, as a condition stricter than the other items. Note that various buttons 1302 such as "Save" on the display screen 1300 is used when an operator performs various operations.

When the signal of the reference material 1106 used to monitor the Z axis returns to the start, another correction operation is performed in a case where signal values of the reference materials 1104 and 1105 are out of a range of values of "drift detection point". At this time, in a case where the signal intensity is augmented or attenuated from all of the reference materials 1104 and 1105 (1203), at least one diagonal pair of reference materials moves by the smallest moving amount so as to reach an amount of θ, in order, based on the information acquired from the scanning before the position having the signal intensity at the time of the start is measured. However, in a case where the position having the signal intensity at the time of the start is not found, at least one diagonal pair of reference materials moves by the smallest moving amount to reach the amount of θ, and moves to a position at which the reference materials have the same signals. At this time, the moving amount, which is obtained by one correction operation, may be set as "θ axis correction range" in FIG. 13. This is performed to reduce the difficulty in correction of the other axes with only one axis too much moving.

Since the correction operation on the θ axis is completed, the drift correction in the X axis or the Y axis is performed in the order of Example 4 using a pair of signals of the diagonal pair of reference materials which has signal intensity with the greatest difference from the signal intensity obtained at the time of the start. Similar to the θ axis, the moving amount by one correction operation may be set for the XY axes. In a case where the drift amount is small, at this time, the signal intensity from all of the reference material returns to the intensity at the time of start, and, as a result, it is possible to acquire a signal having high intensity in a range in which signals from the biological samples passing though the nanopore are limited all the time. At this time, in a case where the peak of the Raman spectrum obtained from the reference material is not present in the same element of the detector at the time of start, the detector moves such that irradiation is performed on the same element and wavenumber correction is performed. Otherwise, the calculation is performed, based on the information of the element in the detector, which has the peak of the Raman spectrum obtained from the reference material at the time of start, and the positional information after the correction, and then the wavenumber correction may be performed. The information of the spectrum for the wavenumber correction may be set to select the material of the reference material, as a setting condition before the measurement. Examples of the materials include a silicon single crystal or molybdenum oxide, tungsten oxide, aluminum oxide, zinc oxide, tin oxide, titanium oxide, or silicon carbide.

In a case where the drift amount is large and the signal intensity from all of the reference materials does not return to the intensity at the time of start, the correction of θ axis and the correction of the XY axes are repeated once more. At this time, the number of times of the repeating may be designated. In a case where the signal intensity at the time of start or the drift detection and the recognized signal intensity are not satisfied within the designated number of times, a warning may be output and remeasurement may be urged. Otherwise, in a case where the signal from the reference material is simply smaller than a determined value, a warning may be output and remeasurement may be urged. The warning is effective in the detection in a case where a significant shift occurs due to a large influence when there is an unexpected collision to the sequencer or the like.

On the other hand, when the scanning is ended after the installation of the sequencer, the measurement is started, and the signal of the reference material 1106 used to perform the Z-axis correction returns to the start, another correction operation is performed in a case where signal values of the reference materials 1104 and 1105 are out of the range of values of "drift detection point" (1202). At this time, in a case where the reference materials 1104 and 1105 have the signal intensity of which the augmentation or the attenuation is different between the diagonal pair of two reference materials 1104 or the diagonal pair of two reference material 1105 (1204), estimation is performed such that the drift amounts in the XY-axes directions are the signal intensity at the time of start based on the scanning result before the measurement, and movement is performed. In a case where the estimated results have drift amounts different between the diagonal pair of reference materials, the drift in a θ-axis direction is assumed. Therefore, the XY-axes correction is performed at a position at which the diagonal pair of reference materials has the same signal amount. After the XY-axes correction, at least one diagonal pair of reference materials with the smallest moving amount moves by θ to a position at which the signal intensity at the start is detected.

In a case where the drift amount is small, at this time, the signal intensity from all of the reference material returns to the intensity at the time of start (1205), and, as a result, it is possible to acquire a signal having high intensity in the range in which signals from the biological samples passing though the nanopore are limited all the time, and it is possible to return to the time of start. At this time, in a case where the peak of the Raman spectrum obtained from the reference material is not present in the same element of the detector at the time of start, the detector moves such that irradiation is performed on the same element and wavenumber correction is performed. Otherwise, the calculation is performed, based on the information of the element in the detector, which has the peak of the Raman spectrum obtained from the reference material at the time of start, and the positional information after the correction, and then the wavenumber correction may be performed (1206). Then, the drift correction is completed (1207).

In a case where the drift amount is large and the signal intensity from all of the reference materials returns to the intensity at the time of start, the correction of θ axis and the correction of the XY axes are repeated once more. At this time, the number of times of the repeating may be designated. In a case where the signal intensity at the time of start or the drift detection and the recognized signal intensity are not satisfied within the designated number of times, an alarm may go off (1208 and 1209) and rescanning or remeasurement may be urged. Otherwise, in a case where the signal from the reference material is simply smaller than a determined value, a warning may be output and remeasurement may be urged. The warning is effective in the detection in a case where a significant shift occurs due to a large influence when there is an unexpected collision to the sequencer or the like.

Note that the present invention is not limited to the examples described above, and the present invention may include various modification examples. For example, the examples described above are described detail for easy understanding of the invention, and the invention is not necessarily limited to the example including the entire configurations in the description. In addition, it is possible to replace some configurations in a certain example with configurations in another example, and it is possible to add a configuration in one example to a configuration in another example. In addition, it is possible to perform addition, removal, and replacement of another configuration to, from, and with some configurations in the examples.

Further, a case where the configurations, functions, analyzers, or the like described above are realized with software by generating a program that realizes a part or all thereof is described as an example; however, a part or all thereof may be realized with hardware by designing, for example, an integrated circuit.

As described above, in the specification, embodiments of the present invention is described, based on the various examples; however, the description above discloses many items of invention, in addition to the invention described in Claims. Some of the items are described, as follows.

[Model Example 1]

A position control method and a controller includes: an optical system that is capable of performing irradiation with at least one beam of excitation light;
means that is capable of detecting a signal generated from the irradiation with at least one beam of excitation light; and
position calculating means that simultaneously performs both detection of a measurement sample and detection of a reference material, and calculates a position at which the measurement sample is intensively irradiated with the excitation light, in response to the signal acquired from the reference material, in which the position of the measurement sample is corrected or the position of the optical system is corrected to a desirable position, based on the calculation result.

[Model Example 2]

In the position control method and the controller according to Model Example 1, the signal generated through the irradiation with the excitation light means Raman scattered light or fluorescence.

[Model Example 3]

In the position control method and the controller according to Model Example 1, the detection of the signal is performed from at least one or more reference materials.

[Model Example 4]

In the position control method and the controller according to Model Example 1, a position of the detector or information of an image element is corrected using a spectrum of at least one or more reference materials, which is generated through the irradiation with the excitation light.

[Model Example 5]

In the position control method and the controller according to Model Example 1, a signal is detected from the reference material which is smaller than the sample.

[Model Example 6]

In the position control method and the controller according to Model Example 1, the reference material is irradiated with the excitation light having a spot diameter which is smaller than the sample and the signal is detected from the reference material.

[Model Example 7]

In the position control method and the controller according to Model Example 1, the reference material is irradiated with the excitation light having a spot diameter which is smaller than the sample, with the excitation light having a wavelength which is shorter than that of the sample, and the signal is detected from the reference material.

[Model Example 8]

In the position control method and the controller according to Model Example 1, when the spot diameter of the excitation light is smaller than the sample and the reference material, the spot diameter of the excitation light to the reference material is larger than the spot diameter of the excitation light to the sample, and the signal is detected from the reference material.

[Model Example 9]

In the position control method and the controller according to Model Example 1, the signal is detected from the reference material formed of a silicon single crystal, molybdenum oxide, tungsten oxide, aluminum oxide, zinc oxide, tin oxide, titanium oxide, or silicon carbide.

[Model Example 10]

In the position control method and the controller according to Model Example 1, biomolecules as the sample are analyzed.

[Model Example 11]

The control method and the controller according to Model Example 1, further includes: drive means for driving the positions of the sample and the reference material and an excitation spot position, in which scanning is performed using the drive means and the position of the measurement sample is corrected or the position of the optical system is corrected to a desirable position, based on the calculation result of the position calculating means.

[Model Example 12]

In the control method and the controller according to Model Example 11, detection of the temperature change and the scanning of the positions of the sample and the reference material and the excitation spot position by drive means are simultaneously performed, and the position of the sample is corrected or the position of the optical system is corrected to a desirable position, with the detection of the temperature change.

[Model Example 13]

In the control method and the controller according to Model Example 1, a drift amount and a drift direction are calculated, based on augmentation and attenuation of the signal from the reference material, and the position of the measurement sample is corrected or the position of the optical system is corrected to the desirable position.

[Model Example 14]

In the control method and the controller according to Model Example 13, the drift amount and the drift direction are calculated, based on the position of the reference material and information of the signal intensity, which are acquired in advance, and the augmentation and the attenuation of the signal from the reference material, and the position of the measurement sample is corrected or the position of the optical system is corrected to the desirable position.

[Model Example 15]

In the control method and the controller according to Model Example 1, correction to obtain a desirable position is performed, by using the excitation spot position which matches with the position of the sample, and the reference material disposed at a shifted position.

[Model Example 16]

In the control method and the controller according to Model Example 1, correction to obtain a desirable position is performed, by using the reference material having a focal position which is different from that of the sample.

[Model Example 17]

In the controller according to Model Example 1, a pinhole provided on an optical axis of measurement light of the reference material is smaller than a pinhole provided on an optical axis of the measurement light of the sample.

[Model Example 18]

In the control method and the controller according to Model Example 1, the reference material has a rectangular parallelepiped shape, and correction to a desirable position is performed.

[Model Example 19]

In the control method and the controller according to Model Example 1, long sides of at least two rectangular parallelepiped-shaped reference materials are present to form a shape of orthogonal straight lines, and correction to a desirable position is performed.

[Model Example 20]

In the method and the controller according to Model Example 1, the reference material has plasmon resonance.

REFERENCE SIGNS LIST 100 nanopore Raman DNA sequencer
101 light source
102, 218 objective lens
103 microscope observation container
104 XY stage
105 Z-axis adjusting mechanism
106 filter
107 beam splitter
108 diffraction grafting
109 detector
110 LED
111 two-dimensional detector
112 mirror
113 multi-irradiating mechanism
114 lens
115 drive control part
116 computer
117 near-infrared (NIR) mirror
118 analyzer
201 observation container
202, 302, 402, 702, 904, 1102 nanopore
203, 301 substrate
204 sample introducing compartment
205 sample inlet compartment
206, 207 inlet path
208, 209 outlet path
210, 211 liquid
213 sample
214, 215 electrode
216 conductive thin film
217 liquid immersion medium
302 nanopore
303, 403, 703, 903, 1103 conductive thin film
401, 701, 901, 1000, 1100 multi-nanopore substrate
404, 405, 406, 704, 705, 706, 902, 903, 1001, 1002, 1004~1006 reference material
901 position on substrate which is irradiated with excitation light
1003, 1101 position on substrate which is irradiated with excitation light
1300 display screen
1300 drift correction window

The invention claimed is:

1. A fixed position controller comprising:
an irradiation optical system that is capable of performing simultaneous irradiation with a plurality of beams of excitation light;
a detector that detects a signal generated from an irradiation position through irradiation with the excitation light;
a substrate that is provided with at least one nanopore and at least one reference object; and
a position control unit that calculates a position at which a measurement sample is irradiated with the excitation light, in response to the signal acquired from the reference object when the measurement sample positioned in the nanopore and the reference object are simultaneously irradiated with the excitation light, and that controls a position of the irradiation on the measurement sample with the excitation light based on corresponding calculation results,
wherein the measurement sample is measured while the position of the irradiation with the excitation light is controlled.

2. The fixed position controller according to claim 1, wherein the signal generated through the irradiation with the excitation light means Raman scattered light or fluorescence.

3. The fixed position controller according to claim 1, wherein a position of the detector or information of an image element of the detector is corrected using a spectrum of the reference object, which is generated through the irradiation with the excitation light.

4. The fixed position controller according to claim 1,
wherein the reference object has a diameter which is smaller than that of the measurement sample.

5. The fixed position controller according to claim 1,
wherein the reference object is irradiated with excitation light having a spot diameter which is smaller than a spot diameter of the excitation light with which the measurement sample is irradiated.

6. The fixed position controller according to claim 1,
wherein, when the spot diameter of the excitation light is smaller than those of the measurement sample and the reference object, the spot diameter of the excitation light to the reference object is larger than the spot diameter of the excitation light to the measurement sample.

7. The fixed position controller according to claim 1,
wherein the measurement sample is a biomolecule, and
wherein the reference object is formed of a silicon single crystal, molybdenum oxide, tungsten oxide, aluminum oxide, zinc oxide, tin oxide, titanium oxide, or silicon carbide.

8. The fixed position controller according to claim 1,
wherein the position control unit
scans the spot position of the excitation light with respect to both positions of the measurement sample and the reference object, and
calculates a position on the measurement sample which is intensively irradiated with the excitation light, in response to the signal acquired from the reference object, and controls the spot position on the measurement sample at a desirable position based on the calculation results.

9. The fixed position controller according to claim 8,
wherein the position control unit
detects a predetermined temperature change, then starts to scan the spot position of the excitation light, and controls the spot position at the desirable position.

10. The fixed position controller according to claim 1,
wherein the position control unit
calculates a drift amount and a drift direction in response to information of the position and signal intensity of the reference object obtained in advance and an increase and decrease in the signal acquired from the reference object, and controls the spot position at a desirable position.

11. A fixed position control method comprising:
simultaneously irradiating at least one nanopore and at least one reference object in a substrate with excitation light;
calculating a position at which a measurement sample is irradiated with the excitation light, based on a signal which is generated from the reference object and is detected by a detector; and
measuring the measurement object, while controlling a position of the irradiation on the measurement sample with the excitation light, based on corresponding calculation results.

12. The fixed position control method according to claim 11,
wherein the signal generated through the irradiation with the excitation light means Raman scattered light or fluorescence.

13. The fixed position control method according to claim 11, further comprising:
scanning the spot position of the excitation light with respect to both positions of the measurement sample and the reference object, and
calculating a position at which the measurement sample is intensively irradiated with the excitation light, in response to the signal acquired from the reference object, and controlling the spot position on the measurement sample at a desirable position based on the calculation results.

14. The fixed position control method according to claim 13, further comprising:
detecting a predetermined temperature change, then starting to scan the spot position of the excitation light, and controlling the spot position at the desirable position.

15. The fixed position control method according to claim 11, further comprising:
calculating a drift amount and a drift direction in response to information of the position and signal intensity of the reference object, which is acquired in advance, and an increase and decrease in the signal acquired from the reference object, and controlling the spot position at a desirable position.

* * * * *